US012605196B2

(12) United States Patent
Vogt et al.

(10) Patent No.: US 12,605,196 B2
(45) Date of Patent: Apr. 21, 2026

(54) METHOD AND DEVICE FOR MIXING BONE CEMENT WITH DEPRESSURIZATION

(71) Applicant: Heraeus Medical GmbH, Wehrheim (DE)

(72) Inventors: Sebastian Vogt, Wehrheim (DE); Thomas Kluge, Wehrheim (DE)

(73) Assignee: Heraeus Medical GmbH, Wehrheim (DE)

( * ) Notice: Subject to any disclaimer, the term of this patent is extended or adjusted under 35 U.S.C. 154(b) by 1093 days.

(21) Appl. No.: 17/681,217

(22) Filed: Feb. 25, 2022

(65) Prior Publication Data

US 2022/0296290 A1     Sep. 22, 2022

(30) Foreign Application Priority Data

Mar. 22, 2021    (EP) ..................................... 21164046

(51) Int. Cl.
A61B 17/88        (2006.01)
B01F 23/50        (2022.01)
        (Continued)

(52) U.S. Cl.
CPC ........ A61B 17/8833 (2013.01); B01F 23/511 (2022.01); B01F 23/54 (2022.01);
        (Continued)

(58) Field of Classification Search
CPC ............ A61B 17/8822; A61B 17/8827; A61B 17/8833
See application file for complete search history.

(56) References Cited

U.S. PATENT DOCUMENTS

| | | | |
|---|---|---|---|
| 4,613,326 A | 9/1986 | Szwarc | |
| 4,671,263 A | 6/1987 | Draenert | |
| (Continued) | | | |

FOREIGN PATENT DOCUMENTS

| | | |
|---|---|---|
| DE | 3640279 A1 | 6/1987 |
| DE | 69812726 T2 | 2/2004 |
| (Continued) | | |

OTHER PUBLICATIONS

Charnley, J.: Anchorage of the femoral head prosthesis of the shaft of the femur. J. Bone Joint Surg. 42 (1960) 28-30.
(Continued)

*Primary Examiner* — Elizabeth Insler
(74) *Attorney, Agent, or Firm* — Dicke, Billig & Czaja, PLLC

(57)        ABSTRACT

One aspect is a method for producing a bone cement from monomer liquid and cement powder using a depressurization device. The method is performed using a device comprising a cartridge having a drive piston, and a central piston being permeable to gases and the monomer liquid and impermeable to the cement powder and being arranged between the drive piston and a cartridge head. The method comprising the steps of expelling residual gases into the surroundings of the device by means of the movement of the drive piston; displacing gases between the powder particles with the inflowing monomer liquid; and depressurizing a cavity of the cartridge, by partially removing the contained monomer liquid. The invention also relates to such a device for mixing a bone cement, with a depressurization device.

14 Claims, 17 Drawing Sheets

Figure 1:
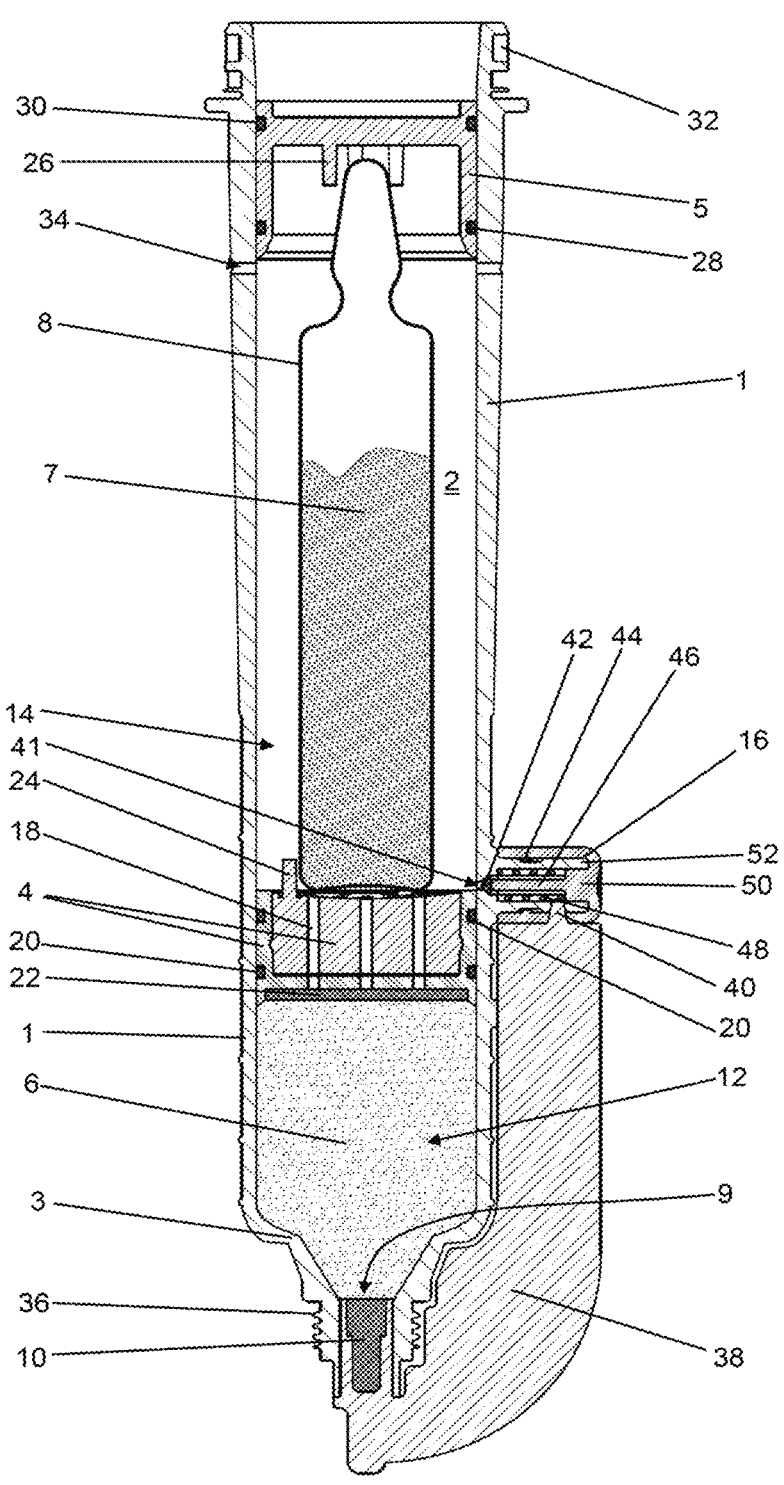

(51) Int. Cl.
    *B01F 35/00*     (2022.01)
    *B01F 35/71*     (2022.01)
    *B01F 35/75*     (2022.01)
    *B01F 101/20*     (2022.01)

(52) U.S. Cl.
    CPC ........ *B01F 35/189* (2022.01); *B01F 35/7131* (2022.01); *B01F 35/7174* (2022.01); *B01F 35/754251* (2022.01); *A61B 2017/8838* (2013.01); *B01F 2101/20* (2022.01)

(56) References Cited

U.S. PATENT DOCUMENTS

| | | | |
|---|---|---|---|
| 4,758,096 | A | 7/1988 | Gunnarsson |
| 4,973,168 | A | 11/1990 | Chan |
| 5,100,241 | A | 3/1992 | Chan |
| 5,344,232 | A | 9/1994 | Nelson et al. |
| 5,586,821 | A | 12/1996 | Bonitati et al. |
| 5,588,745 | A | 12/1996 | Tanaka et al. |
| 5,624,184 | A | 4/1997 | Chan |
| 5,997,544 | A | 12/1999 | Nies et al. |
| 6,033,105 | A | 3/2000 | Barker et al. |
| 6,709,149 | B1 | 3/2004 | Tepic |
| 2012/0155214 | A1 | 6/2012 | Faccioli et al. |
| 2018/0132917 | A1 | 5/2018 | Vogt et al. |
| 2018/0132919 | A1 | 5/2018 | Vogt et al. |
| 2018/0256233 | A1* | 9/2018 | Vogt .................... B01F 35/7131 |
| 2018/0289406 | A1 | 10/2018 | Vogt et al. |
| 2018/0310974 | A1 | 11/2018 | Vogt et al. |
| 2018/0333176 | A1 | 11/2018 | Vogt et al. |

FOREIGN PATENT DOCUMENTS

| | | |
|---|---|---|
| DE | 102009031178 B3 | 9/2010 |
| DE | 102017113126 A1 | 12/2018 |
| EP | 0692229 A1 | 1/1996 |
| EP | 0796653 A2 | 9/1997 |
| EP | 1005901 A2 | 6/2000 |
| EP | 1016452 A2 | 7/2000 |
| EP | 1020167 A2 | 7/2000 |
| EP | 1886647 A1 | 2/2008 |
| EP | 3320869 B1 | 5/2019 |
| EP | 3320870 B1 | 7/2019 |
| EP | 3505237 A1 | 7/2019 |
| WO | 94/26403 A1 | 11/1994 |
| WO | 97/18031 A1 | 5/1997 |
| WO | 99/67015 A1 | 12/1999 |

OTHER PUBLICATIONS

Search Report mailed Sep. 9, 2021 by the European Patent Office for priority European patent application No. 21164046.1.

\* cited by examiner

METHOD AND DEVICE FOR MIXING BONE CEMENT WITH DEPRESSURIZATION

CROSS-REFERENCE TO RELATED APPLICATIONS

This application claims priority to European Patent Application No. 21164046.1, filed on Mar. 22, 2021, the entirety of which is incorporated herein by reference.

The invention relates to a method for producing a bone cement from a monomer liquid and a cement powder as starting components of the bone cement.

The invention also relates to a device for producing a bone cement, in particular a pasty polymethyl methacrylate bone cement, from a monomer liquid and a cement powder.

Polymethyl methacrylate (PMMA) bone cements date back to the fundamental works by Sir Charnley (Charnley, J.: Anchorage of the femoral head prosthesis of the shaft of the femur. J. Bone Joint Surg. 42 (1960) 28-30.). Conventional polymethyl methacrylate bone cements (PMMA bone cements) are composed of a powdered component and a liquid monomer component (K.-D. Kühn: "*Knochenzemente für die Endoprothetik: Ein aktueller Vergleich der physikalischen und chemischen Eigenschaften handelsüblicher PMMA-Zemente*" [Bone cements for endoprosthetics: a current comparison of the physical and chemical properties of commercially available PMMA cements]. Springer-Verlag Berlin Heidelberg New York, 2001). The monomer component generally contains the monomer methyl methacrylate and an activator (N,N-dimethyl-p-toluidine) dissolved therein. The powder component, here referred to as cement powder or else as bone cement powder, comprises: one or more polymers that are produced by polymerization, preferably suspension polymerization, based on methyl methacrylate and comonomers, such as styrene, methyl acrylate, or similar monomers; an x-ray opacifier; and the initiator dibenzoyl peroxide. Upon mixing the powder component with the monomer component, a plastically deformable dough—the actual bone cement or bone cement dough—is produced by swelling of the polymers of the powder component in the methyl methacrylate. Upon mixing the powder component with the monomer component, the activator N,N-dimethyl-p-toluidine reacts with dibenzoyl peroxide to form radicals. The formed radicals initiate the radical polymerization of the methyl methacrylate. As the polymerization of the methyl methacrylate progresses, the viscosity of the bone cement dough increases until it solidifies.

PMMA bone cements can be mixed in suitable mixing cups with the aid of spatulas by mixing the cement powder with the monomer liquid. The inclusion of air bubbles in the bone cement dough may thereby occur, which can negatively influence the mechanical properties of the hardened bone cement.

In order to avoid air inclusions in the bone cement dough, a plurality of vacuum cementing systems have been described, of which the following are cited by way of example: U.S. Pat. Nos. 6,033,105 A, 5,624,184 A, 4,671,263 A, 4,973,168 A, 5,100,241 A, WO 99/67015 A1, EP 1 020 167 A2, U.S. Pat. No. 5,586,821 A, EP 1 016 452 A2, DE 36 40 279 A1, WO 94/26403 A1, EP 1 005 901 A2, EP 1 886 647 A1, U.S. Pat. No. 5,344,232 A.

A development in cement technology is represented by cement systems in which both the cement powder and the monomer liquid are already packaged in separate compartments of the mixing devices, and are mixed with one another only immediately before the cement application in the cement system. Such sealed, fully prepackaged mixing systems have been proposed with EP 0 692 229 A1, DE 10 2009 031 178 B3, U.S. Pat. Nos. 5,997,544 A, 6,709,149 B1, DE 698 12 726 T2, EP 0 796 653 A2, U.S. Pat. No. 5,588,745 A, US 2018/333 176 A1, US 2018/310 974 A1, US 2018/289 406 A1, US 2018/132 919 A1, US 2018/132 917 A1, and US 2018/256 233 A1.

Patent DE 10 2009 031 178 B3 discloses a storage and mixing device as a fully prepackaged mixing system in which the starting components necessary for producing the bone cement dough are already stored in the storage and mixing device and can be combined and mixed in the storage and mixing device.

Polymethyl methacrylate bone cements are used as bone cement dough in the not-yet-hardened, pasty state after mixing the cement powder with the liquid monomer component. Given use of mixing devices, the bone cement dough is located in a cartridge in the event of powder-liquid cements. In the production of such conventional PMMA bone cements, after mixing the two starting components, the bone cement dough that is formed is extruded with the aid of manually operable extrusion devices. The bone cement dough is pushed out of the cartridge by moving a discharge piston.

For extrusion, these simple mechanical extrusion devices use, in particular, clamping rods which are driven by a rocker arm which is to be manually actuated. The manually driven extrusion devices have been tried-and-tested for decades worldwide and have, until now, represented the state of the art.

In patents EP 3 320 869 B1 and EP 3 320 870 B1, a cement system is described in which the mixing of the monomer liquid with the cement powder takes place by injecting monomer liquid into compressed cement powder. In private practical experiments, it was shown that polymethyl methacrylate bone cement dough can be reliably produced using this device. Sometimes, fluctuations in the monomer liquid volume in the monomer liquid container can lead to unwanted injections of minuscule volumes of monomer liquid into the swollen cement dough during the extrusion of the formed bone cement. These injections are in the volume range of a few microliters.

The object of the present invention is to overcome the disadvantages of the prior art. In particular, the object of the invention is the development of a method and a device in which a re-pressing of monomer liquid after the cement powder has been wetted with the monomer liquid can be avoided. The device should be as simple as possible to operate and cost-effective to manufacture. The method should be easily applicable and cost-effective to realize. The device should in particular be suitable and provided for realizing the method.

The object of the invention is thus the development of a method and a device for producing bone cement, in particular for mixing and discharging polymethyl methacrylate bone cement, based on the teachings of patent specifications EP 3 320 869 B1 and EP 3 320 870 B1, which can be produced simply and cost-effectively and by means of which an optimally homogeneous bone cement is to be produced. The method to be developed should be designed in such a way that an unwanted injection of minuscule volumes of monomer liquid into the formed cement dough during the extrusion process is reliably prevented. Furthermore, the cement device and the method should also be developed such that an injection of even small and minuscule volumes of monomer liquid into the bone cement can be reliably avoided during the discharge of the formed bone cement.

The objects of the invention are achieved by a method for producing a bone cement, in particular a pasty polymethyl methacrylate bone cement, wherein the bone cement is produced from a cement powder and a monomer liquid using a device for mixing the bone cement, the device comprising a) a cartridge having a cylindrical interior, b) a cement powder for producing the bone cement, c) a monomer liquid for producing the bone cement, wherein the monomer liquid is contained in a monomer liquid container, d) a cartridge head having a discharge opening for expelling the bone cement, wherein the cartridge head closes off the cylindrical interior of the cartridge at a front side of the cartridge except for the discharge opening, e) a closure, wherein the closure is permeable to gases and impermeable to powder particles of the cement powder, and wherein the closure is arranged in the discharge opening and is removable from the discharge opening, f) a drive piston, wherein the drive piston is impermeable to gases and the monomer liquid, wherein the drive piston is arranged movable towards the cartridge head in the cylindrical interior of the cartridge, g) a central piston, wherein the central piston is permeable to gases and the monomer liquid and impermeable to the powder particles of the cement powder, wherein the central piston is arranged movably in the cylindrical interior of the cartridge towards the cartridge head and is arranged between the drive piston and the cartridge head, wherein the central piston separates the cylindrical interior of the cartridge into a first cavity and a second cavity, wherein the first cavity is delimited on a front side by the cartridge head and the closure, opposite thereto by the central piston, and laterally by an inner wall of the cartridge, and wherein the second cavity is delimited on a front side by the central piston, opposite thereto by the drive piston, and laterally by the inner wall of the cartridge, wherein the cement powder is arranged in the first cavity, and wherein the monomer liquid container is arranged in the second cavity, wherein the method comprises the following steps:

A) moving the drive piston toward the cartridge head,

B) opening the monomer liquid container or rupturing the monomer liquid container via the movement of the drive piston toward the cartridge head, and thereby releasing the monomer liquid in the second cavity, C) expelling residual gases through the central piston, through the cement powder, and through the closure, into the surroundings of the device, by means of the movement of the drive piston, D) injecting the monomer liquid through the central piston into the cement powder by further moving the drive piston toward the cartridge head, E) displacing gases between the powder particles with the inflowing monomer liquid, wherein the gases escape through the closure into the surroundings of the device, F) wetting the powder particles of the cement powder, and G) depressurizing the second cavity after steps A) to F), wherein the second cavity is depressurized by partially removing the monomer liquid contained in the second cavity.

The closure is preferably permeable to gases and to the monomer liquid.

The cylindrical interior of the cartridge has a cylindrical geometry, optionally except for the asymmetries caused by a depressurization device or the connection to the depressurization device, for example by at least one groove in an inner wall of the cartridge or by at least one connection in the cartridge to a reservoir for the monomer liquid. The cylindrical shape is the simplest by means of which the interior of the cartridge can be realized. A cylindrical shape is understood to mean, in geometrical terms, the shape of a general cylinder with an arbitrary base, i.e., not only a cylinder with a circular base. The inner wall of the interior of the cartridge can thus be formed by the cylinder shell of a cylinder with arbitrary base, in particular with different bases, i.e., also with non-circular or non-round bases. According to the invention, however, a cylindrical geometry with a rotationally symmetrical and in particular circular base is preferred for the cylindrical interior of the cartridge, since this is the easiest to manufacture.

According to the invention, it can be provided that the cement powder is compacted in the first cavity.

The drive piston is preferably arranged movably in the cylindrical interior of the cartridge along the cylinder axis of the cylindrical interior.

The central piston is preferably arranged between the drive piston and the cartridge head movably in the cylindrical interior of the cartridge along the cylinder axis of the cylindrical interior.

"Impermeable to powder particles" means that at least a majority of the mass of the powder particles of which the cement powder consists, cannot trickle through or fall through. Preferably, at least 90% of the mass of the powder particles of which the cement powder consists, cannot trickle through or fall through. Particularly preferably, at least 99% of the mass of the powder particles of which the cement powder consists, cannot trickle through or fall through. Most particularly preferably, at least 99.9% of the mass of the powder particles of which the cement powder consists, cannot trickle through or fall through. The percentile fractions thereby relate to the total mass of the cement powder, and not to the total number of powder particles of the cement powder.

Depressurization can occur with the aid of a depressurization device specifically provided for this purpose, which is also preferred according to the invention. Alternatively, however, depressurization can also take place by, for example, deforming the drive piston or the central piston, or by retracting or drawing back the drive piston, or by absorbing a portion of the monomer liquid with an absorbent material, for example a sponge-like material such as a cellulose or such as a pulp.

It can be provided that the pressure in the second cavity is reduced via the depressurizing by at least 30%, particularly preferably is reduced by at least 60%, most particularly preferably is reduced by at least 90%.

It is hereby ensured that, in the second cavity, a pressure reduction is achieved which significantly reduces or largely prevents a re-pressing of monomer liquid from the second cavity into the first cavity. Methods for determining the absolute pressure in the second cavity are known to the person skilled in the art. The pressure is mediated as hydrostatic pressure with the remainder of the monomer liquid in the second cavity, and can be measured as such in the customary manner known to the person skilled in the art. To this end, for example, for experimental purposes an electronic pressure sensor can or will be attached to the inner wall of the second cavity (in the compressed state), which sensor is electrically contacted through a hole in the cartridge wall of the cartridge.

Furthermore, it can be provided that the movement of the drive piston toward the cartridge head is driven by an external extrusion device, wherein the device for mixing the bone cement is preferably inserted into the extrusion device and/or is attached to the extrusion device.

The drive pistons of several devices for mixing the bone cement can hereby be driven effectively in succession with the same extrusion device. The extrusion device can be purely mechanically driven, motor-driven, or also with driven a compressed gas.

Furthermore, it can be provided that the powder particles of the cement powder are completely wetted by the monomer liquid in step F).

It is hereby ensured that a homogeneous bone cement is produced, and that the depressurization in step G) takes place only when the cement powder has been completely wetted by the monomer liquid.

Furthermore, it can be provided that the method comprises the following chronological steps:

H) removing the closure from the cartridge head after step G), and

I) extruding the bone cement out of the first cavity and through the discharge opening via a movement of the central piston toward the cartridge head, wherein the central piston is pressed by the drive piston toward the cartridge head.

Via these steps, the bone cement is provided for further use. For example, following step I), the bone cement is useable for a medical application. Likewise, for example, the bone cement is collectible in a vessel from which a medical application can thereafter take place. By contrast, step I) alone does not enable any medical application, since no contact of the bone cement with a human or animal body takes place.

Following the extrusion according to step I), the bone cement dough can be applied. The bone cement can be pressed into a collection tray or applied to an implant before implanting said implant.

In particular, it can also be provided that the method is not used for medical, diagnostic, or therapeutic treatment of a human or animal body.

It is hereby clarified that the method is not a medical method, in particular is not a medical method excluded from being patented.

It can further be provided that depressurization in step G) takes place via a manual or automatic actuation of a depressurization device of the device for mixing the bone cement, wherein preferably the automatic actuation of the depressurization device is triggered by a movement of the drive piston and/or is triggered by a movement of the closure out of the cartridge head, and is particularly preferably driven by the movement of the closure out of the cartridge head.

The implementation of the method and the use of the device are hereby simplified. The movement of the closure is preferably driven by the bone cement as soon as said cement has become free-flowing on account of being wetted with monomer liquid.

It can thus be provided that depressurization, or an automatic depressurization device, is driven and triggered by the movement of the closure out of the cartridge head. The closure only moves out of the cartridge head if the entirety of the cement powder has been wetted with the monomer liquid. The interconnection of the unwetted powder particles of the cement powder with one another prevents an axial movement of the closure prior thereto. In its movement toward the cartridge head, the drive piston can then move the opened or burst monomer liquid container and the central piston toward the cartridge head. For this purpose, the closure may be connected to a valve system which closes at least one continuous connection in the cartridge wall. Upon a movement of the closure out of the cartridge head, the valve system is thereby opened so that depressurization is achieved by the escape of the monomer liquid from the second cavity through the at least one continuous connection.

Furthermore, it can be provided that, during depressurization in step G), the monomer liquid is discharged into a reservoir outside the cartridge or in the cartridge wall, wherein the reservoir is preferably sealed tightly to the outside for the monomer liquid; or, during depressurization in step G), the monomer liquid is conducted into a reservoir within the drive piston, into a reservoir on the side of the drive piston opposite the second cavity, and/or into a reservoir laterally between the drive piston and the cartridge, wherein, preferably in the latter case, the monomer liquid is conducted via at least one groove in an inner wall of the cartridge, past a front sealing ring of the drive piston, into the reservoir laterally between the drive piston and the cartridge, when a forward sealing ring of the drive piston is pushed over or onto the at least one groove.

It is sufficient for a small proportion (less than 2 ml) of the monomer liquid to be discharged from the second cavity to achieve depressurization in the second cavity. With said reservoirs, a rapid and straightforward diversion of the monomer liquid from the second cavity can be achieved. At the same time, the reservoirs can be closed off to the outside, thus preventing release of the monomer liquid into the surroundings of the device. In this context, "to the outside" means into the environment of the device.

According to a preferred development, it can be provided that, during the depressurization in step G), the monomer liquid is not conducted into the first cavity; it is preferably conducted into at least one reservoir separate from the first cavity, wherein particularly preferably the at least one reservoir is arranged outside the cartridge, within the cartridge wall, within the drive piston, on the side of the drive piston opposite the second cavity, and/or laterally between the drive piston and the cartridge.

It is hereby prevented that portions of the monomer liquid enter the first cavity during the depressurization and change the composition of the bone cement in areas there. In addition, effective and complete depressurization can thus take place.

It can also be provided that, during the depressurization in step G), the second cavity is filled with the open or ruptured monomer liquid container and with residues of the monomer liquid.

It is hereby clarified that the hydrostatic overpressure building up in the second cavity may occur by removing the monomer liquid from the second cavity.

The objects underlying the present invention are also achieved by a device for mixing a bone cement, the device comprising a) a cartridge having a cylindrical interior, b) a cement powder for producing the bone cement, c) a monomer liquid for producing the bone cement, wherein the monomer liquid is contained in a monomer liquid container, d) a cartridge head having a discharge opening for expelling the bone cement, wherein the cartridge head closes off the cylindrical interior of the cartridge at a front side of the cartridge except for the discharge opening, e) a closure, wherein the closure is permeable to gases and impermeable to powder particles of the cement powder, and wherein the closure is arranged in the discharge opening and is removable from the discharge opening, f) a drive piston, wherein the drive piston is impermeable to gases and the monomer liquid, wherein the drive piston is arranged movably towards the cartridge head in the cylindrical interior of the cartridge, g) a central piston, wherein the central piston is permeable to gases and the monomer liquid and impermeable to the powder particles of the cement powder, wherein the central piston is arranged movably in the cylindrical interior of the cartridge toward the cartridge head and is arranged between the drive piston and the cartridge head, wherein the central piston separates the cylindrical interior of the cartridge into a first cavity and a second cavity, wherein the first cavity is delimited on a front side by the cartridge head and the closure, opposite thereto by the central piston, and laterally by an inner wall of the cartridge, and wherein the second cavity is delimited on a front side by the central piston, opposite thereto by the drive piston, and laterally by the inner wall of the cartridge, wherein the cement powder is arranged in the first cavity, and wherein the monomer liquid container is arranged in the second cavity, and h) a depressurization device by means of which monomer liquid is dischargeable from the second cavity or is dischargeable from the second cavity and receivable, or by means of which the volume of the second cavity is increasable, wherein the depressurization device is connected or connectible to the second cavity.

An enlargement of the volume of the second cavity can be achieved, for example, by compression of the central piston and/or of the drive piston, or by expansion of the wall of the cartridge in the region of the second cavity, or by pulling the second cavity apart, for example in that the cartridge is constructed in two parts, wherein the two parts are connected to one another in the region of the second cavity by means of a screw connection, so that the second cavity is extended by rotating by a few degrees.

It can be provided that a pulp is used to receive the monomer liquid from the second cavity, which pulp at least partially, preferably completely, absorbs the monomer liquid.

It can be provided that the depressurization device has a hollow connecting piece that extends from the outer surface of the cartridge, wherein the hollow connecting piece preferably forms an extension of the at least one continuous connection or extends over a thin wall of the cartridge that is pierceable by a spike of the depressurization device.

The depressurization device can have a cap which, at least in an unlocked state, is movable against the cartridge, in particular against the hollow connecting piece (if present). The cap can preferably be used to move a spike, a seal, and/or to manually drive a screw movement.

It can be provided that the device is suitable for realizing a method according to the invention.

The device hereby has the advantages mentioned with respect to the method.

Furthermore, it can be provided that the depressurization device is connected to the second cavity via at least one continuous connection in a wall of the cartridge, wherein the at least one continuous connection is closed or is closeable with at least one sealing body, wherein the at least one sealing body is preferably pressed against the at least one continuous connection with an externally manually operable screw or screw cap, with a rod, or with a spring guide rod.

A simple and cost-effective depressurization device can hereby be provided that is easily and reliably operable from the outside.

It can thereby be provided that the at least one sealing body, or a rod or a spring guide rod pressing onto the at least one sealing body, is liftable from the at least one continuous connection with a spring; preferably, the spring presses the spring guide rod, which presses the at least one sealing body against the at least one continuous connection, away from the at least one continuous connection, wherein the spring is particularly preferably locked with a pin or with a fork-shaped supporting body, and the pin or the fork-shaped supporting body is firmly connected to the closure such that, when the closure moves out of the discharge opening, the pin or the fork-shaped supporting body is also automatically removed from the depressurization device and the locking of the spring is thereby released.

A stable and easy-to-open closure of the at least one continuous connection is hereby provided. An automatic opening of the at least one continuous connection can be achieved via the development.

When the monomer liquid is pressed through the drive piston and through the central piston into the compacted cement powder, the monomer liquid reaches the movable closure in the discharge opening in the cartridge head. Only cement powder wetted with monomer liquid is displaceable or is able to flow within the cartridge due to the action of pressure. The closure is only pushed by the cement powder wetted with the monomer liquid when the entirety of the cement powder is wetted. The closure then moves out of the discharge opening. The closure is connected to a supporting body that is pulled through the closure toward the cartridge head. The supporting body blocks the support of a spring that presses on a sealing body via a spring guide rod. When the supporting body is pulled through the closure toward the cartridge head, the supporting body can no longer support the spring. The spring loses its tension and can no longer press on the sealing body. The sealing body comes loose and releases the previously closed opening in the cartridge wall. The pressurized residual quantity of monomer liquid emerges. The monomer liquid which has emerged can be captured by absorbent material, such as cellulose or disks of paper. After the at least one continuous connection is opened in the cartridge wall, a pressure equalization takes place between the second cavity between the top side of the drive piston and the bottom side of the central piston and the surrounding atmosphere.

In a further embodiment variant, the at least one continuous connection through the cartridge wall can be reversibly closed or closable by a sealing body, wherein the sealing body is pressed against the hole by a spring via a spring guide rod, wherein the spring is supported on a fork-shaped supporting body and the supporting body is connected to the movable closure.

It can also be provided that at least one continuous connection is arranged in the cartridge wall and connects the cylindrical interior of the cartridge to the external surroundings, wherein the at least one continuous connection is reversibly closed or closable, and wherein the reversible closure of the at least one continuous connection takes place via a sealing body which is pressed against the at least one continuous connection by a screw or a screw cap, wherein the screw or the screw cap is manually rotatable from the outside.

The screw or the screw cap is preferably screwed into or onto a hollow connecting piece which is arranged on a shell surface of the cartridge and has an internal thread. The continuous connection in the cartridge wall may be arranged such that the connecting piece surrounds the continuous connection. The screw or the screw cap may press a sealing body against the continuous connection in the cartridge wall. The continuous connection can thereby be closed in a pressure-resistant manner. For depressurization, the screw or the screw cap can be rotated somewhat out of its seat. The sealing body is thereby disengaged and moves back from the at least one continuous connection. The overpressurized monomer liquid emerges. Advantageously, an absorbent material which absorbs small volumes of emerging monomer liquid is arranged behind the sealing body in the depressurization device.

The sealing body can also be pressed against the continuous connection in the cartridge wall by a wedge to be manually removed, or by a cam on a manually rotatable axis.

Furthermore, it can be provided that the depressurization device has a spike for piercing a wall of the cartridge in the region of the second cavity, wherein the spike is movably mounted against the cartridge, wherein the spike is a hollow spike with a cannula that is connected to a reservoir for receiving the monomer liquid, or, after piercing the wall of the cartridge, the spike is manually retractable or retractable by a spring such that it exposes a passage pierced with the spike to discharge the monomer liquid from the second cavity, wherein the wall is preferably thinner in the region of the spike than in the rest of the cartridge.

Given this variant, it is ensured that the second cavity is completely sealed against the depressurization device prior to the wall of the cartridge being pierced with the spike. According to the invention, the spike can have a gutter through which the monomer liquid can flow from the second cavity into the depressurization device.

According to the invention, it can be provided that at least a part of the cartridge wall is so thin that it can be pierced by a spike, wherein the spike can be manually displaced from the outside toward the cartridge wall and, after piercing the cartridge wall, the tip of the spike is retracted from the interior of the cartridge by manual force or by a restoring force of at least one spring. After the cartridge wall has been pierced, a pressure equalization takes place between the second cavity—between the top side of the drive piston and the bottom side of the central piston—and the surrounding atmosphere or a reservoir in the interior of the depressurization device.

It is also possible that the at least one continuous connection is closed with a metal membrane that is pierceable by the manual movement of the spike.

Furthermore, it can be provided that the drive piston is sealed with at least one sealing ring against the inner wall of the cartridge, preferably is sealed with two sealing rings against the inner wall of the cartridge, wherein the two sealing rings are spaced apart from one another, particularly preferably spaced apart from one another by at least 5 mm, in a direction parallel to the cylinder axis of the cylindrical interior.

It is hereby ensured that the monomer liquid is pressed from the second cavity into the first cavity before depressurization and cannot, before depressurization, already be pressed into an intermediate space between the drive piston and the cartridge and, through this intermediate space, past the drive piston.

It can also be provided that at least one groove is arranged in an inner wall of the cartridge which delimits the second cavity, wherein the at least one groove in a direction parallel to the cylinder axis of the cylindrical interior is at least as long as the diameter of a front sealing ring of the at least one sealing ring arranged closest toward the cartridge head, preferably at least twice as long as the front sealing ring, or wherein the at least one groove parallel to the cylinder axis of the cylindrical interior is at least half as long as the front sealing ring and is at least 4 mm wide, preferably at least 8 mm wide, along the cylinder shell.

A depressurization device is hereby realized which is particularly simple and cost-effective to produce, which is automatically activated by traversing the at least one groove with the sealing ring or the front sealing ring of the drive piston.

In a further embodiment of the device, it can be provided that, for self-acting or automatic depressurization, at least one tangential groove which has an axial extension which is at least half the height of the sealing ring of the drive piston is arranged on the inner wall of the cartridge. This means that the drive piston runs at a defined axial position within the cartridge when driving against the central piston. The sealing ring of the drive piston thereby drives onto the tangential groove. The remaining monomer liquid upstream of the drive piston and downstream of the bottom side of the central piston is pressurized.

When the sealing ring or the front sealing ring of the drive piston moves onto the groove, the sealing ring can expand into the groove and the compressive stress of the sealing ring decreases. The pressurized monomer liquid can thereby flow around the sealing ring located in the region of the groove. The pressure of the monomer liquid is thereby reduced. It is advantageous if a second sealing ring is attached to the drive piston at a spacing of at least 5 mm. The emerging monomer liquid is then collected in the space between the shell surface of the drive piston and the inner wall of the cartridge, which space is delimited by the upper sealing ring and lower sealing ring. The shell surface of the drive piston can advantageously contain one or more grooves in order to receive the monomer liquid which emerges when the upper sealing ring is traversed.

It can also be provided that the depressurization device is realized by a compressible drive piston and/or by a compressible central piston, and/or the depressurization device enables an expansion of the wall of the cartridge in the region of the second cavity, and/or enables an axial extension in the region of the second cavity with respect to the cylinder axis of the cylindrical interior.

The depressurization device can hereby be arranged inside the device and takes up no additional space, at least outside the cartridge. The depressurization device is thereby not susceptible to faults and damage due to external mechanical effects.

The invention is based on the surprising finding that depressurizing the monomer liquid in the second cavity after wetting the cement powder makes it possible in the remainder of the method, even given pressure on the drive piston, to prevent further monomer liquid from being injected into the bone cement, and to thereby achieve an improvement in the homogeneity of the produced bone cement, even if drive pistons with a large diameter of more than 25 mm are used. The invention is also based on the surprising finding that, in particular given drive pistons having a large diameter, such large hydrostatic forces can occur due to the pressure bearing on the monomer liquid that monomer liquid can press into the already wetted and swollen cement powder and there lead to monomer liquid inclusions in the bone cement, or to a bone cement with a differing consistency.

The invention is based on the observation that, in those cementing systems manufactured according to EP 3 320 869 B1 and EP 3 320 870 B1, after the drive piston has been driven onto the burst remains of the monomer liquid container and the central piston, a restoring force is exerted on the monomer liquid residues in the space between the top side of the drive piston and the bottom side of the central piston via radial deformation of the cartridge wall. As a result, the remaining monomer liquid in this chamber is pressurized. Surprisingly, it was found in practical experiments that, after mixing of the cement powder with the monomer liquid, a depressurization of the cavity between the top side of the drive piston and the bottom side of the central piston by at least partially removing remaining monomer liquid inclusions prevents the injection of minuscule volumes of monomer liquid into the bone cement which is already forming or has already formed.

An exemplary and preferred method according to the invention for producing a bone cement may be implemented with a device for producing a bone cement, the device comprising a) a hollow-cylindrical cartridge, b) a cartridge head having a discharge opening, c) a closure which is permeable to gases and liquids and impermeable to powder particles, and is arranged so as to be axially movable in the discharge opening, d) a central piston which is permeable to gases and liquids and impermeable to powder particles, and is arranged so as to be axially movable in the interior of the cartridge, e) a first cavity which is delimited by the inner wall of the cartridge, the closure, and the top side of the central piston, f) compressed bone cement powder in the first cavity, g) a drive piston which is arranged below the central piston, and which is impermeable to gases and liquids and which is axially movable in the interior of the cartridge, h) a second cavity which is delimited by the bottom side of the central piston, the inner wall of the cartridge, and the top side of the drive piston, and i) a monomer liquid container which is arranged in the second cavity, wherein the method is characterized by the following successively proceeding steps A) moving the drive piston toward the cartridge head via an external drive device, B) destroying the monomer liquid container via the axial movement of the drive piston toward the cartridge head, C) expressing the residual air through the central piston, through the cement powder, and through the closure into the surrounding atmosphere, D) injecting the monomer liquid through the central piston into the cement powder, by further axially moving the drive piston toward the cartridge head, E) displacing the air between the cement powder particles, F) completely wetting the cement powder particles, G) depressurizing the second cavity, which is filled with the burst monomer liquid container and with residues of the monomer liquid and is delimited by the bottom side of the central piston, the top side of the drive piston and the inner wall of the cartridge, by at least partially removing the monomer liquid included in the second cavity, H) removing the closure from the cartridge head, and I) extruding the bone cement via the axial movement of the drive piston and of the central piston toward the cartridge head.

According to the invention, it can be provided that the depressurization takes place by manually actuating a depressurization device or via an automatic depressurization device.

Given manual depressurization, the monomer liquid is discharged into a reservoir outside the cartridge. A complete pressure equalization with the surrounding atmosphere is thereby preferably produced.

Given self-acting or automatic depressurization, the monomer liquid is conducted into a reservoir within or below the drive piston and/or a reservoir to the side of the drive piston. A partial or even complete pressure equalization with the surrounding atmosphere is thereby achieved.

The exemplary device according to the invention for producing bone cement, in particular for mixing and for discharging polymethyl methacrylate bone cement, may comprise a) a hollow-cylindrical cartridge, b) a cartridge head having a discharge opening, c) a closure which is permeable to gases and liquids and impermeable to powder particles of the cement powder, and is arranged so as to be axially movable in the discharge opening, d) a central piston which is permeable to gases and liquids and impermeable to powder particles, and is arranged so as to be axially movable in the interior of the cartridge, e) a first cavity which is delimited by the inner wall of the cartridge, the closure, and the top side of the central piston, f) compressed bone cement powder in the first cavity, g) a drive piston which is arranged below the central piston, and which is impermeable to gases and liquids and is axially movable in the interior of the cartridge, h) a second cavity which is delimited by the bottom side of the central piston, the inner wall of the cartridge, and the top side of the drive piston, i) a monomer liquid container which is arranged in the second cavity, and j) a depressurization device with which monomer liquid is dischargeable from the second cavity, between the bottom side of the central piston and the top side of the drive piston.

Figure 2:
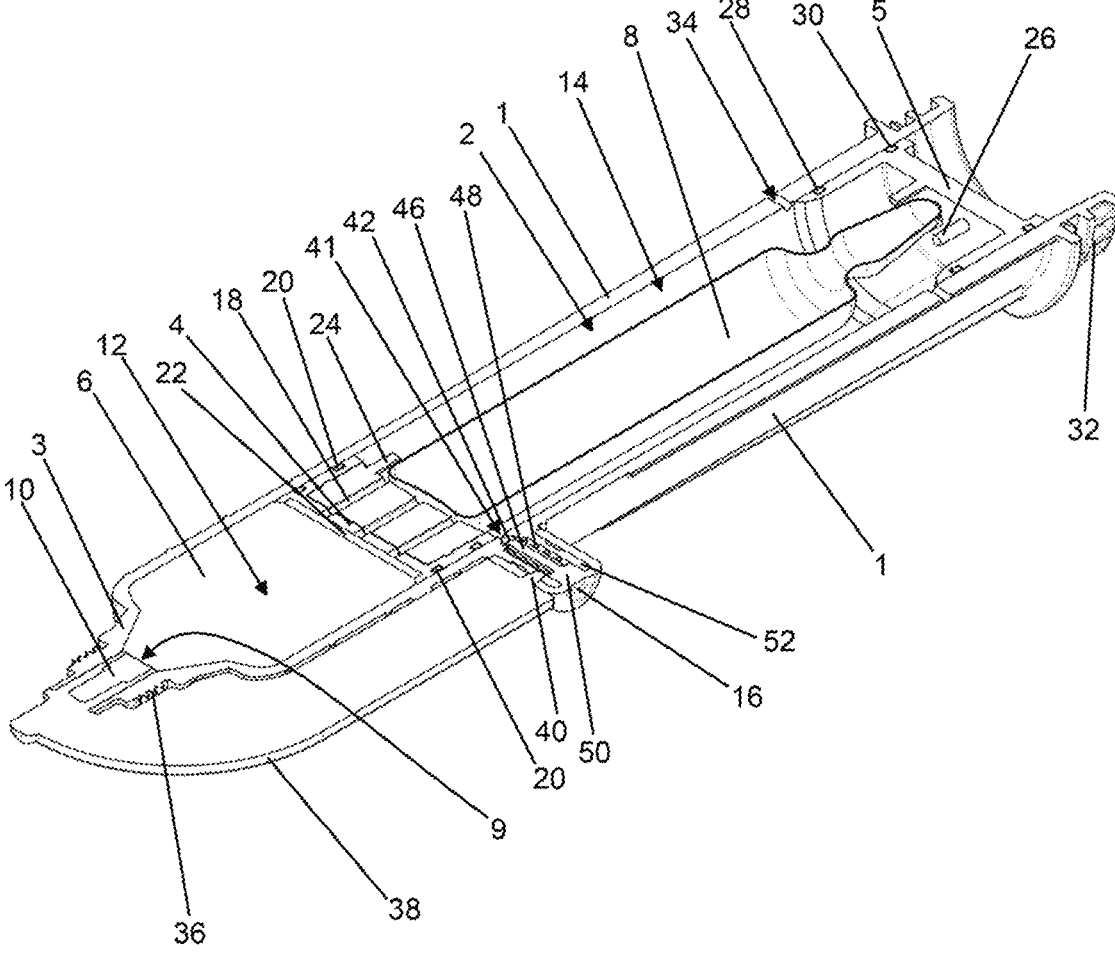
Figure 3:
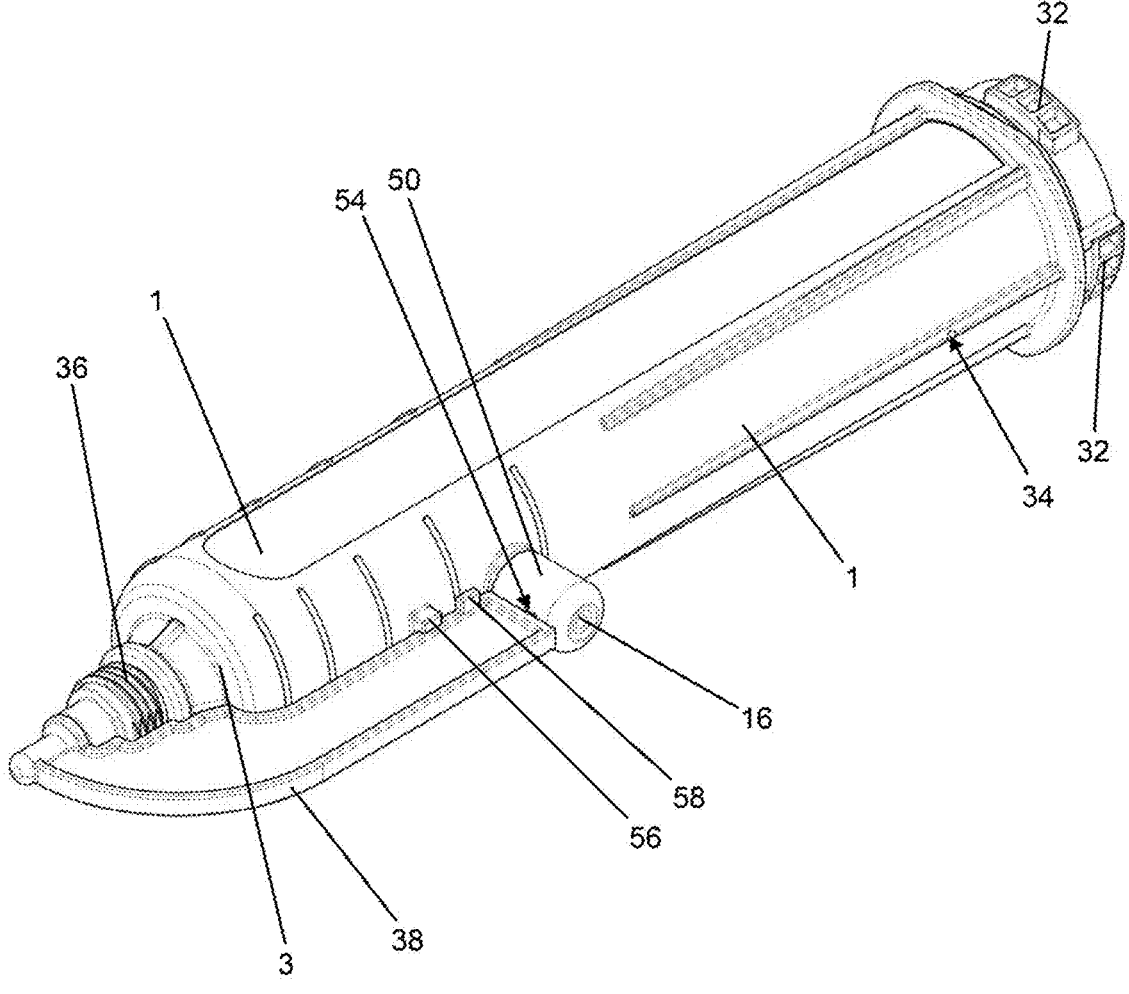
Figure 4:
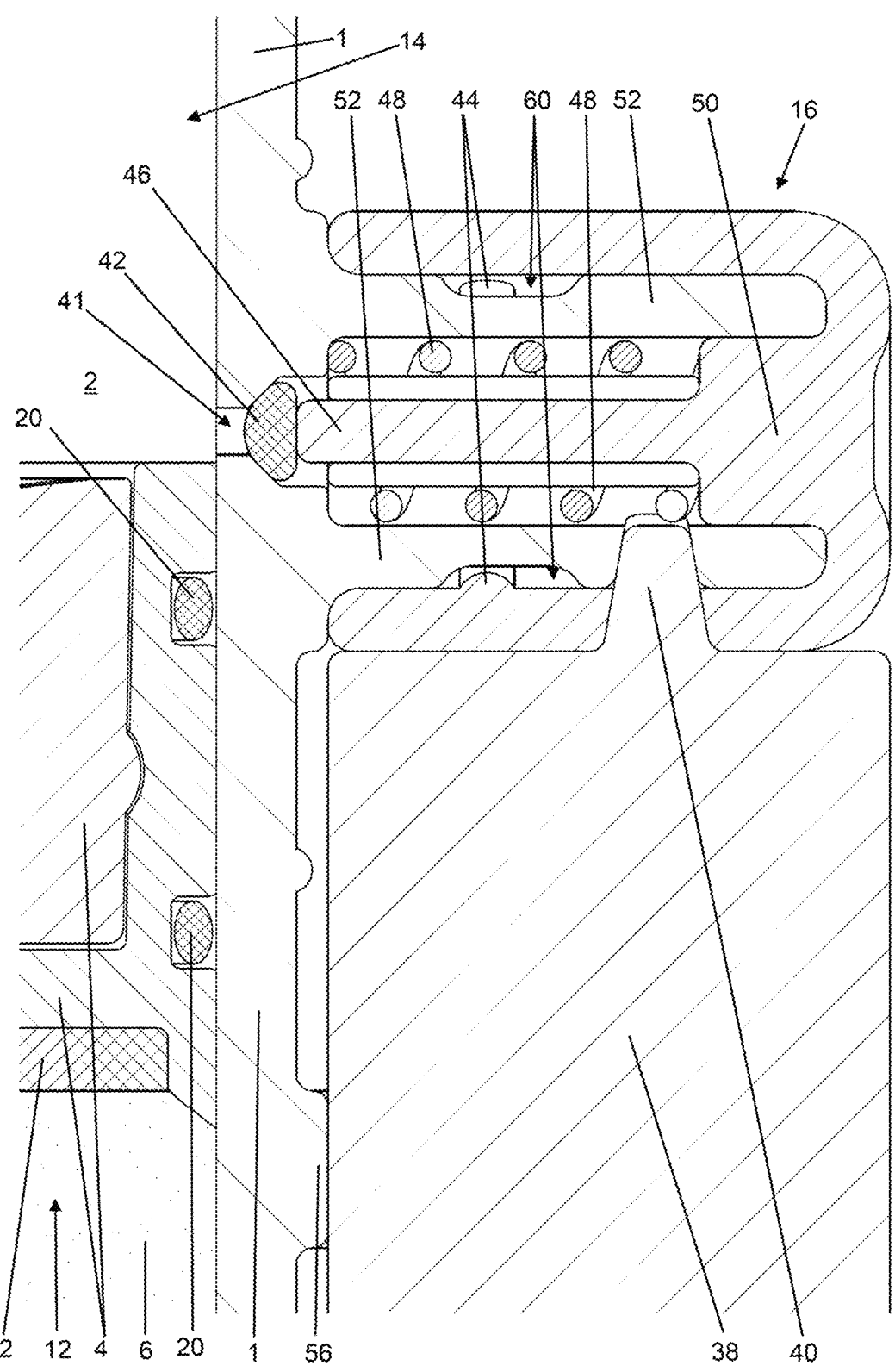
Figure 5:
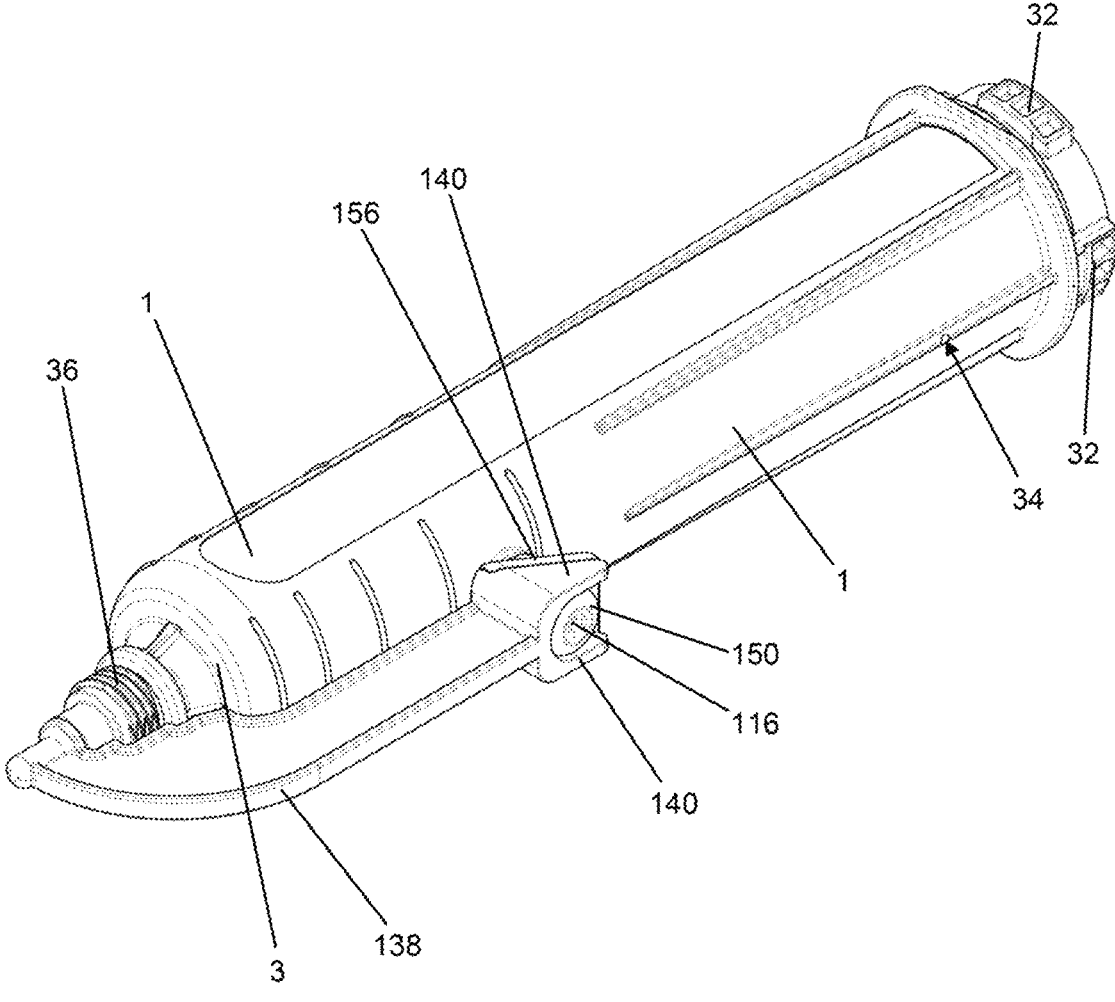
Figure 6:
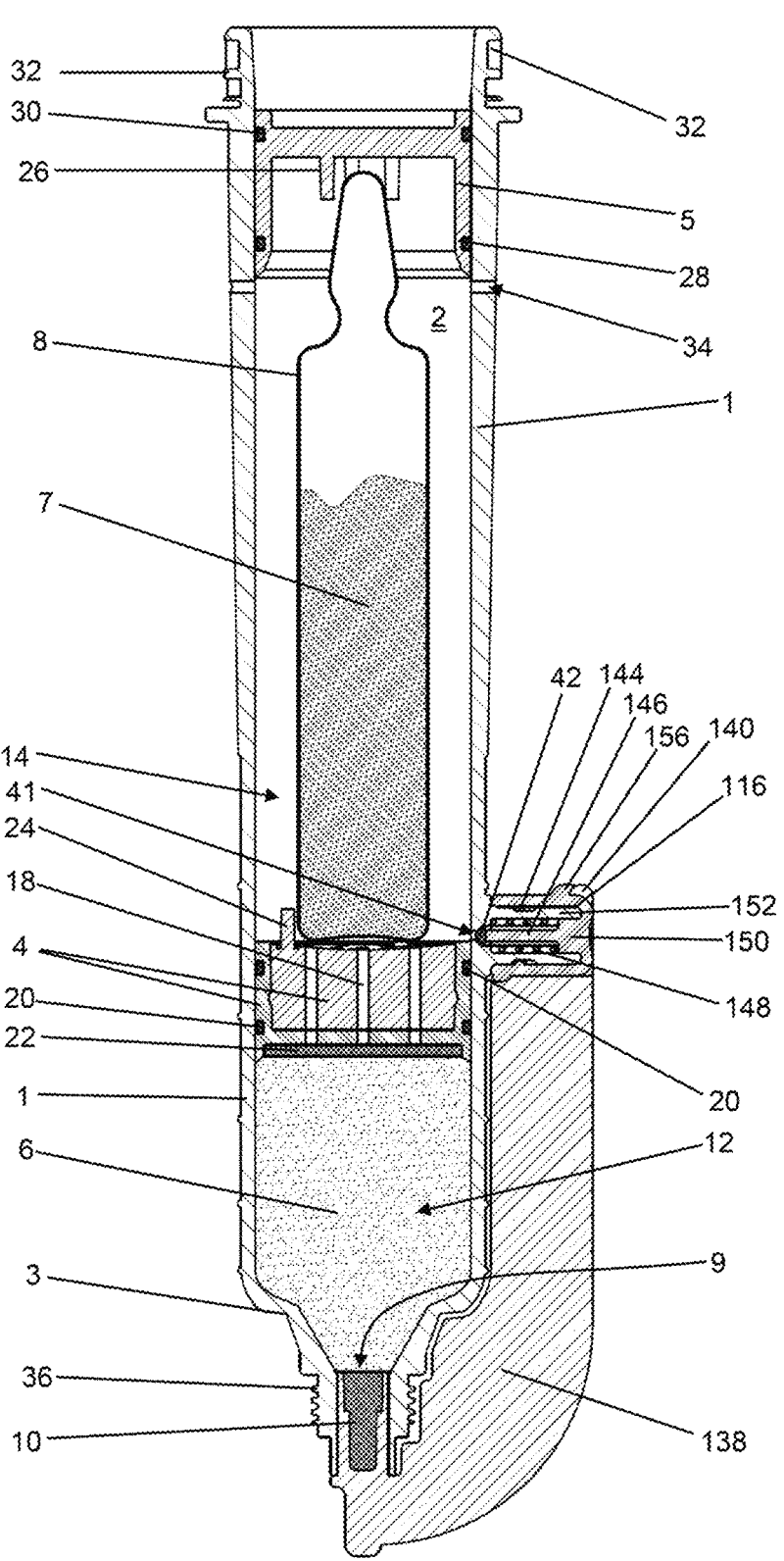
Figure 7:
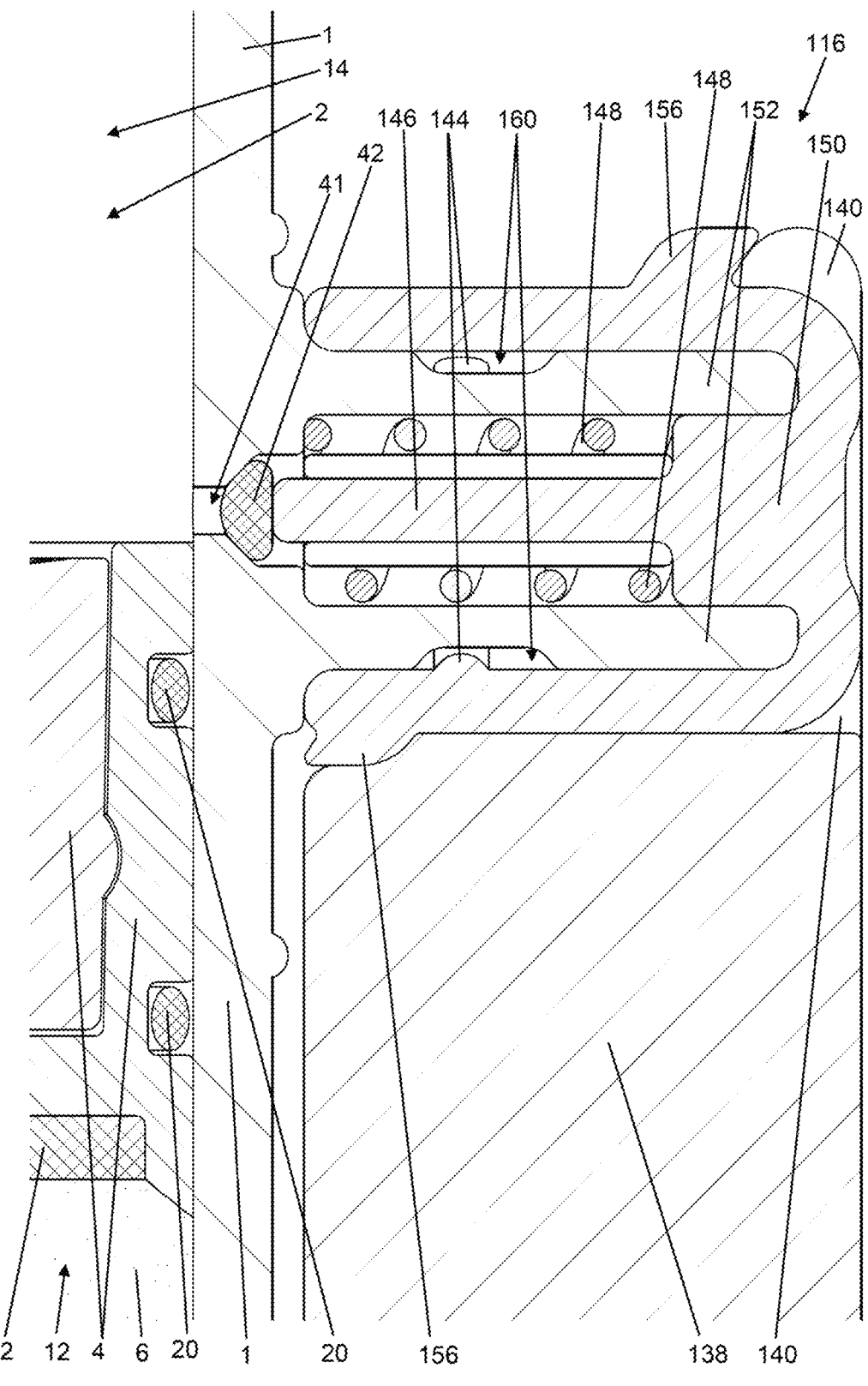
Figure 8:
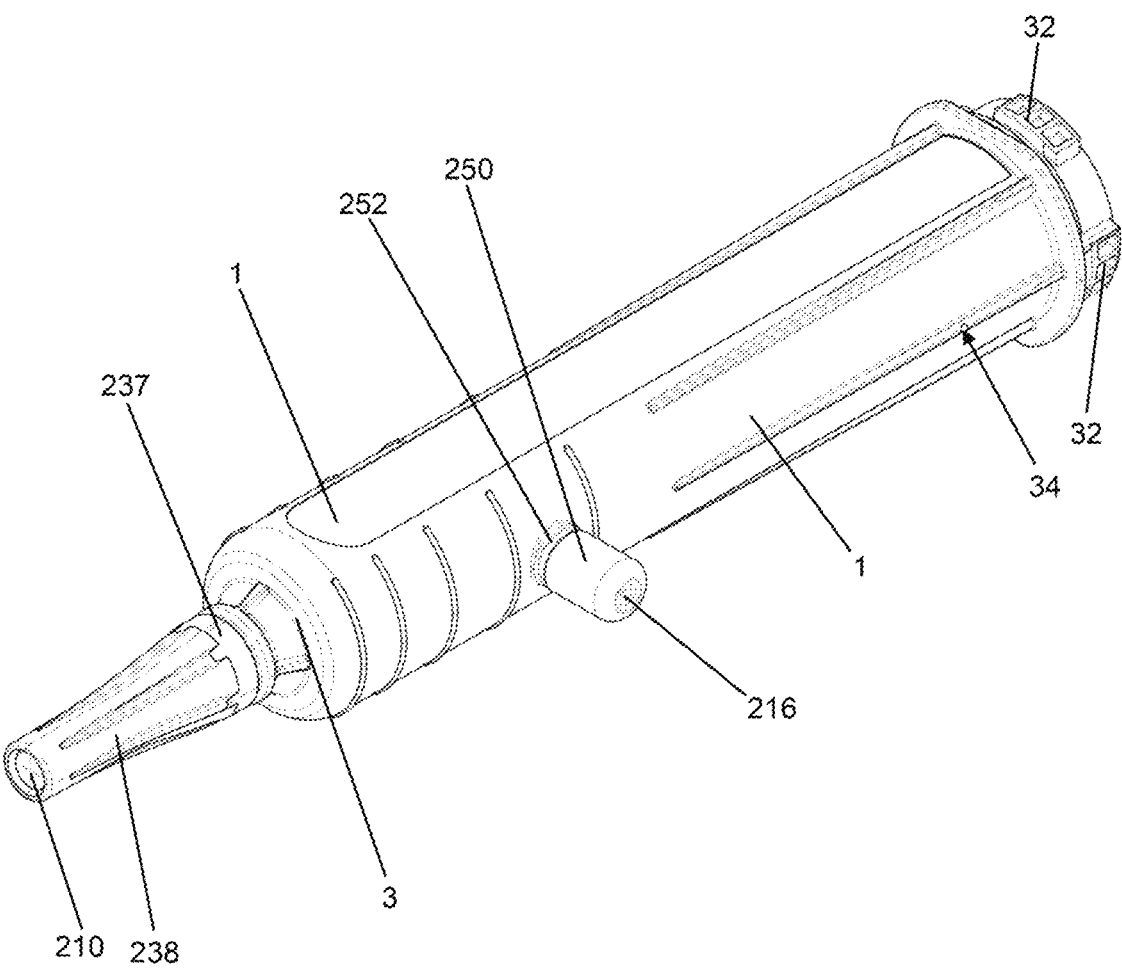
Figure 9:
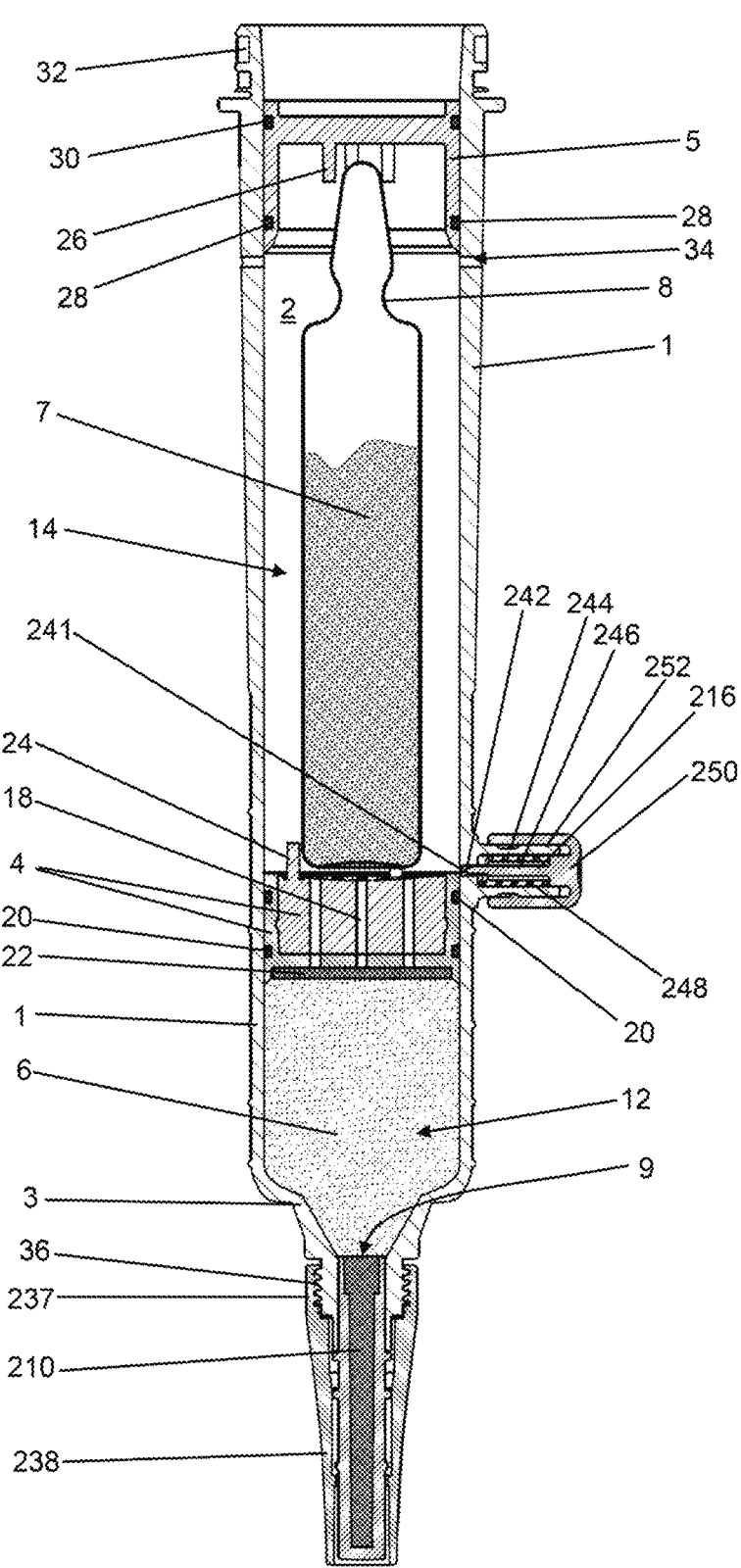
Figure 10:
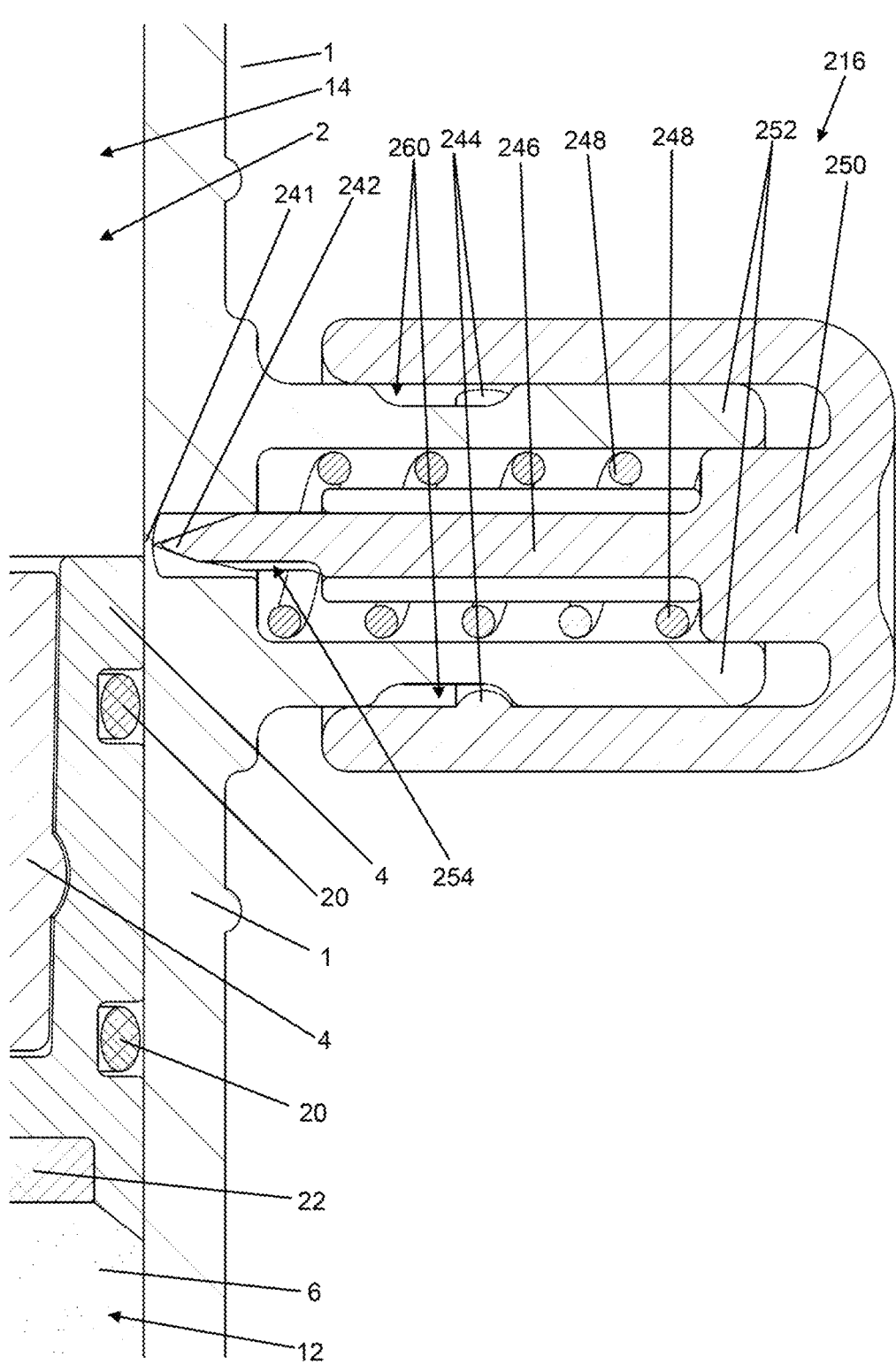
Figure 11:
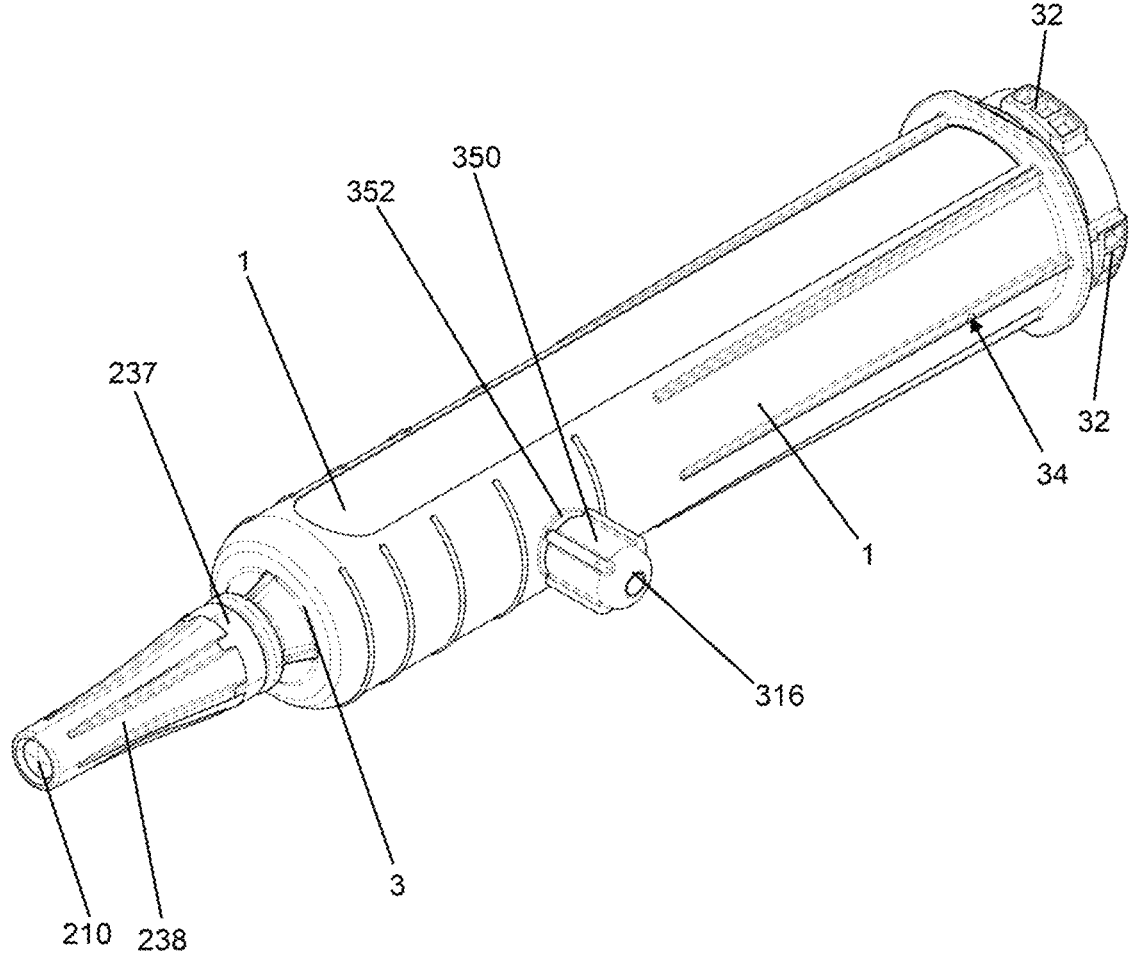
Figure 12:
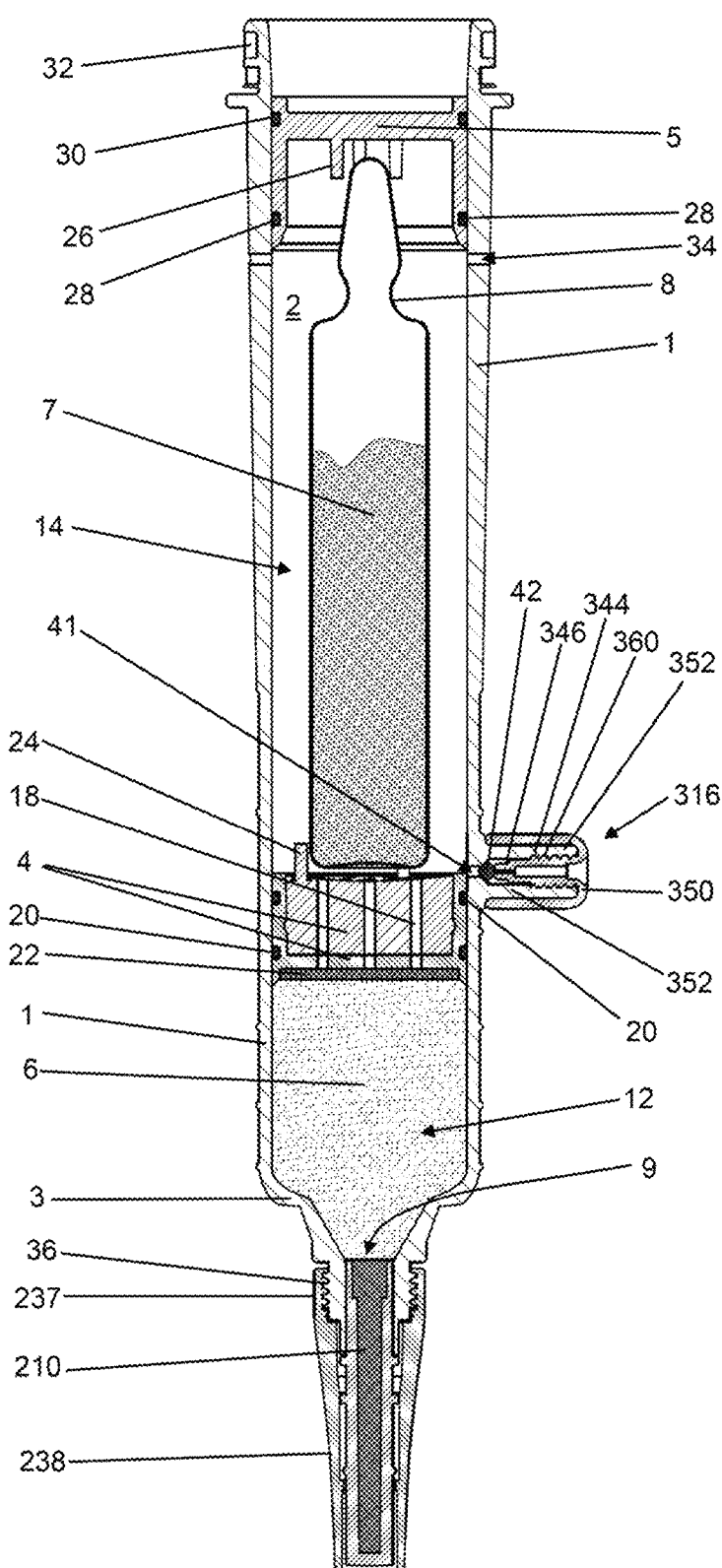
Figure 13:
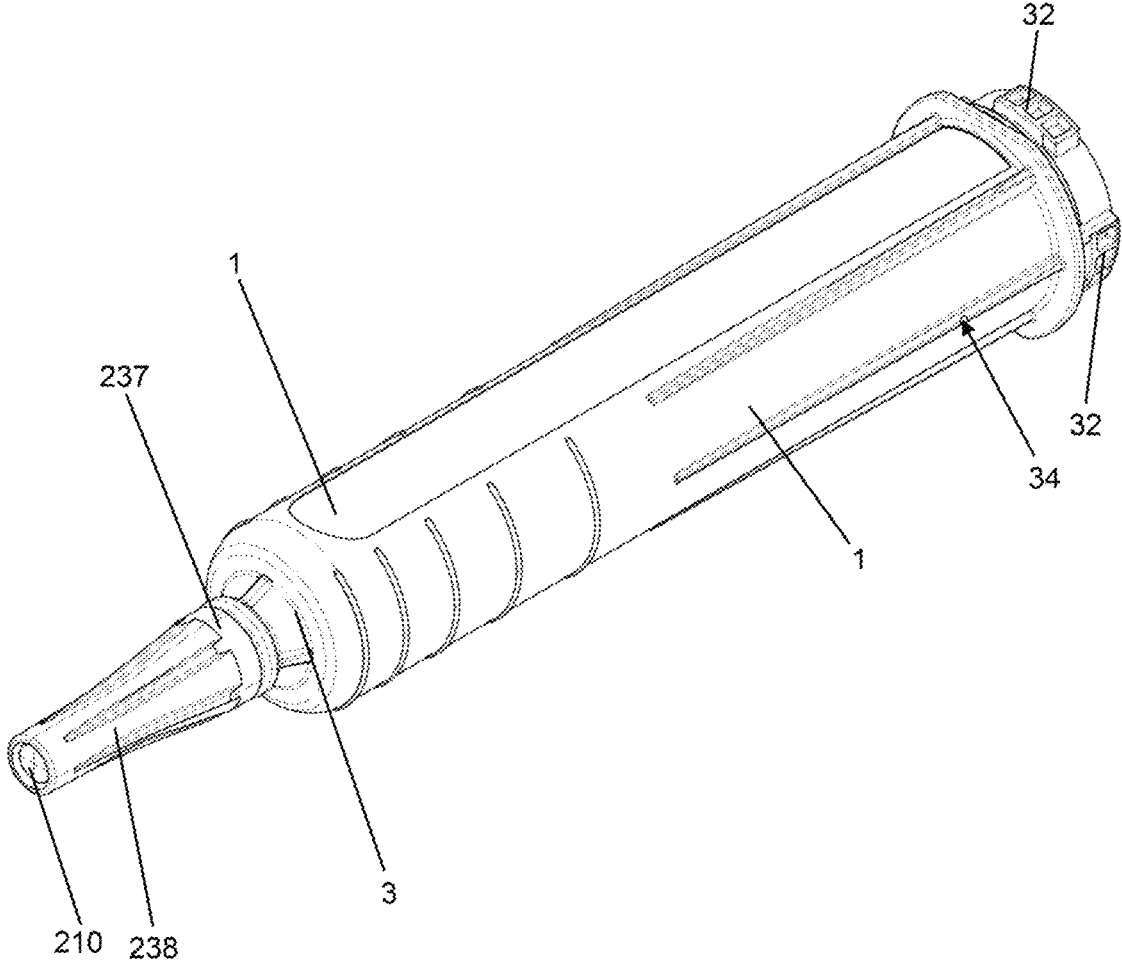
Figure 14:
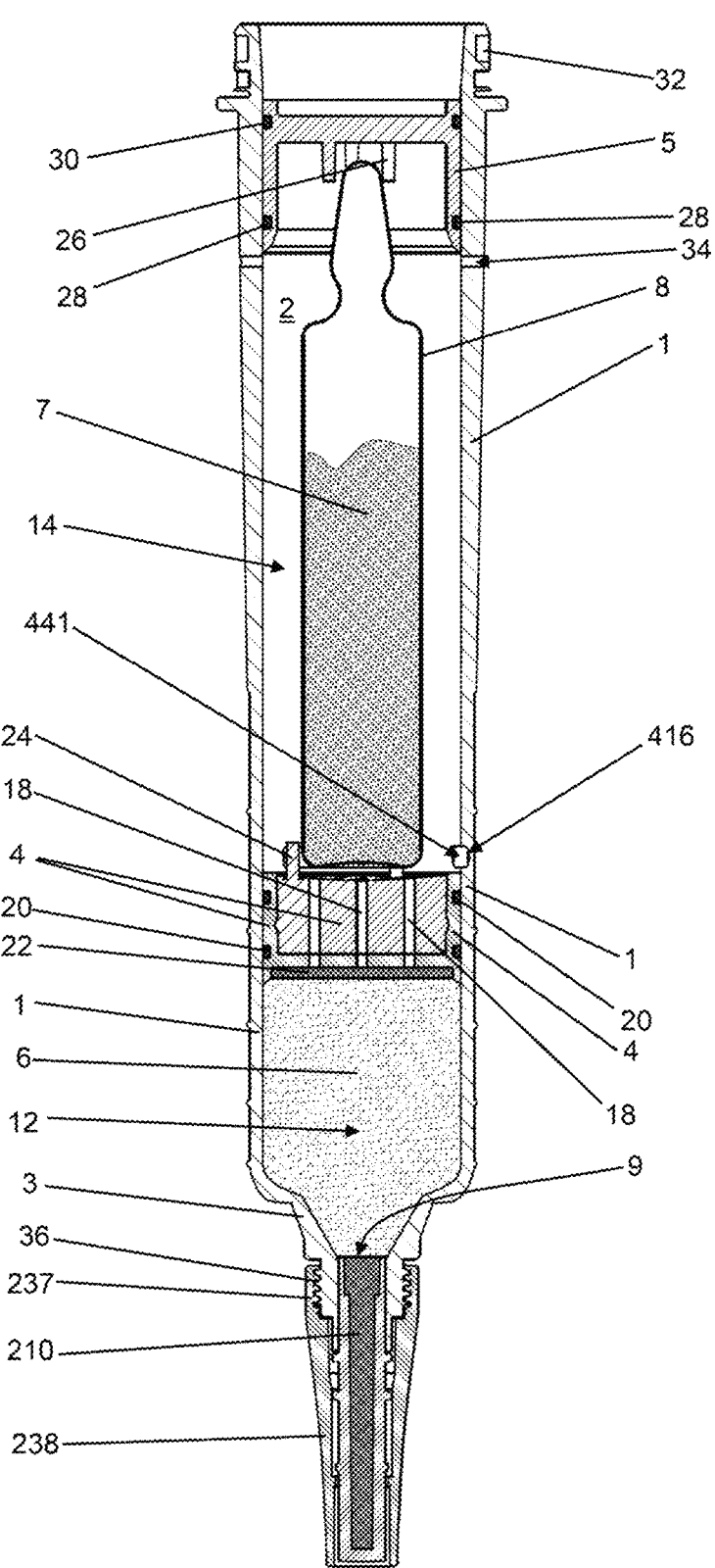
Figure 15:
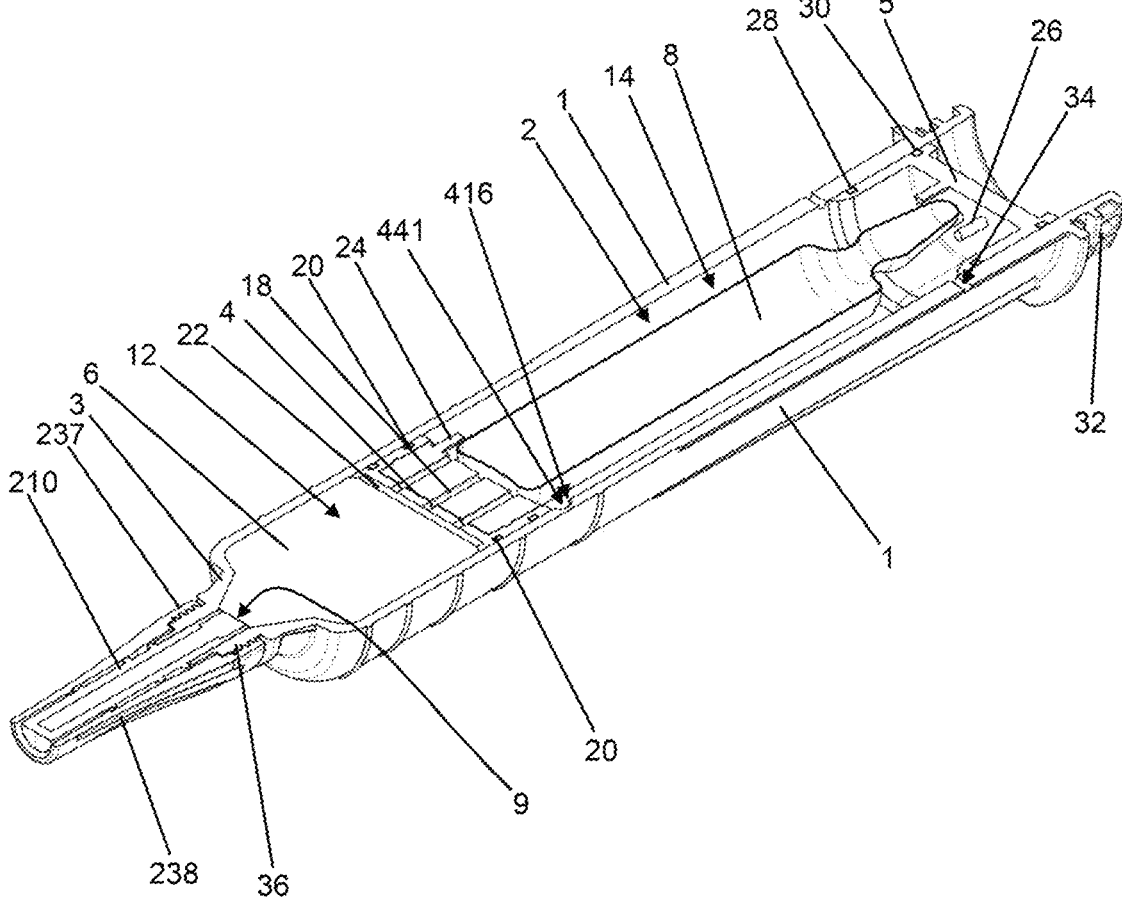
Figure 16:
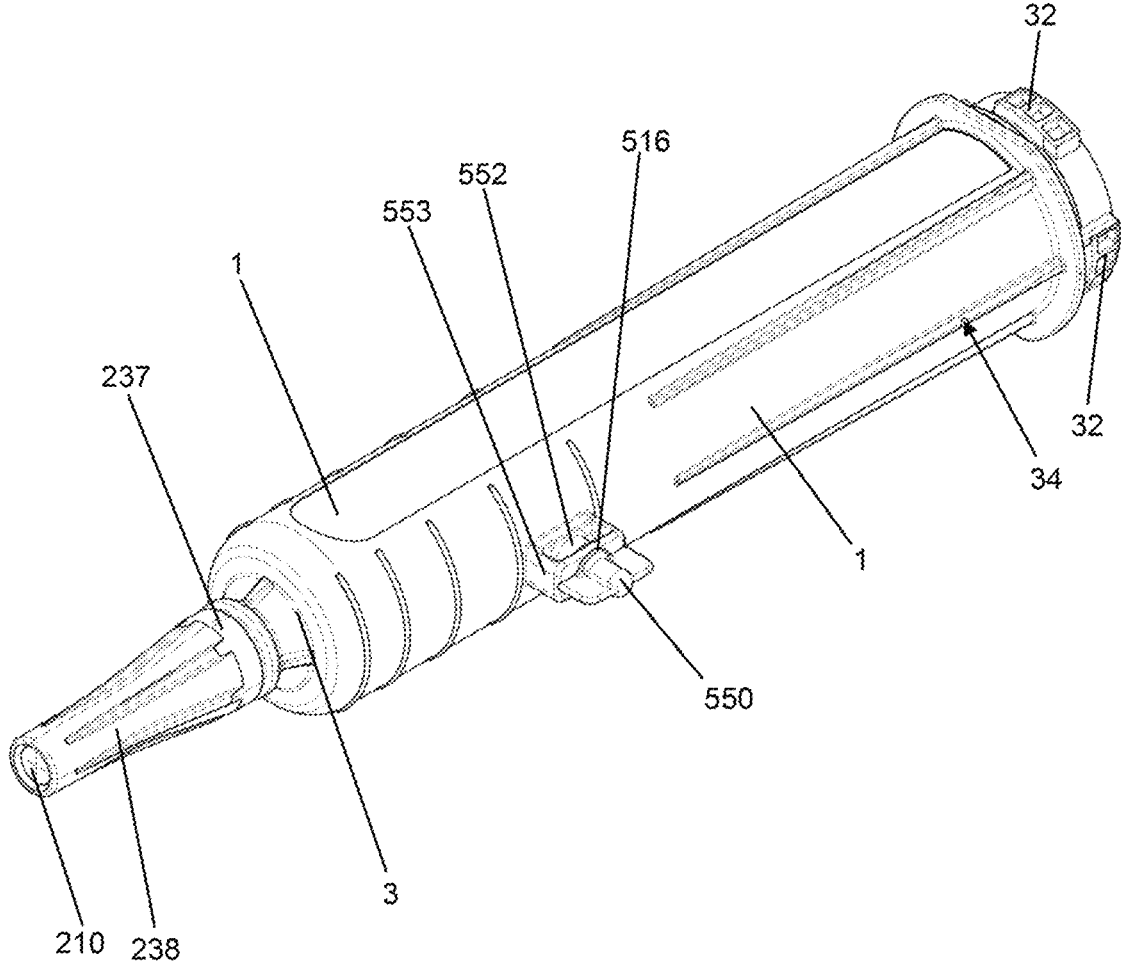
Figure 17:
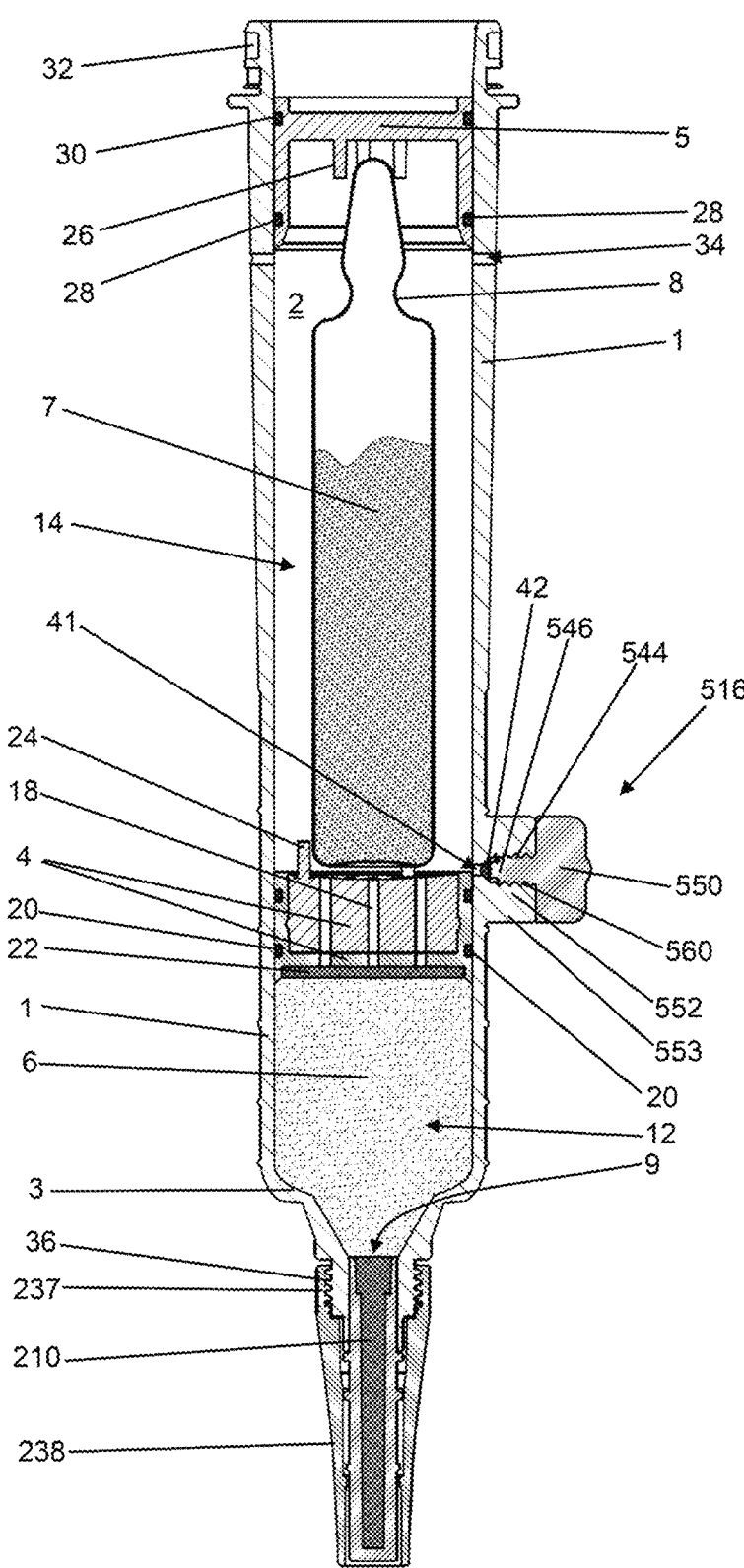

Further exemplary embodiments of the invention are explained below using seventeen schematically depicted Figures, but without thereby limiting the invention. Thereby shown are:

FIG. 1: a schematic cross-sectional view of a first exemplary device according to the invention for producing a bone cement;

FIG. 2: a schematic, perspective cross-sectional view of the first exemplary device according to the invention according to FIG. 1;

FIG. 3: a schematic, perspective external view of the device according to FIGS. 1 and 2;

FIG. 4: an enlarged detail of the cross-sectional view of the first exemplary device according to the invention according to FIG. 1;

FIG. 5: a schematic, perspective external view of a second exemplary device according to the invention for producing a bone cement;

FIG. 6: a schematic cross-sectional view of the second exemplary device according to the invention according to FIG. 5;

FIG. 7: an enlarged detail of the cross-sectional view of the second exemplary device according to the invention according to FIG. 5;

FIG. 8: a schematic, perspective external view of a third exemplary device according to the invention for producing a bone cement;

FIG. 9: a schematic cross-sectional view of the third exemplary device according to the invention according to FIG. 8;

FIG. 10: an enlarged detail of the cross-sectional view of the third exemplary device according to the invention according to FIG. 8;

FIG. 11: a schematic, perspective external view of a fourth exemplary device according to the invention for producing a bone cement;

FIG. 12: a schematic cross-sectional view of the fourth exemplary device according to the invention according to FIG. 11;

FIG. 13: a schematic, perspective external view of a fifth exemplary device according to the invention for producing a bone cement;

FIG. 14: a schematic cross-sectional view of the fifth exemplary device according to the invention according to FIG. 13;

FIG. 15: a schematic, perspective cross-sectional view of the fifth exemplary device according to the invention according to FIGS. 13 and 14;

FIG. 16: a schematic, perspective external view of a sixth exemplary device according to the invention for producing a bone cement; and FIG. 17: a schematic cross-sectional view of the sixth exemplary device according to the invention according to FIG. 16.

In the exemplary embodiments, the same reference numbers are used in part for similar regions, parts, and components of different devices in order to improve the comparability of the exemplary embodiments and to simplify readability. The different exemplary embodiments of the different devices are nevertheless to be understood as completely separate devices that are not converted into one another by a modification.

Shown in FIGS. 1 to 4 are illustrations of a first device according to the invention for producing a bone cement. FIGS. 1 to 3 show various schematic overall views of the first exemplary device according to the invention, and FIG. 4 shows an enlarged detail of the cross-sectional view according to FIG. 1.

According to the first exemplary embodiment of the present invention, the device can have a tubular cartridge 1 made of a plastic with a cylindrical interior 2, which is closed on its front side (at the bottom in FIG. 1 and at the bottom left in FIGS. 2 and 3) by a cartridge head 3. The cartridge head 3 preferably likewise consists of a plastic. A central piston 4 mounted so as to be movable toward the cartridge head 3 (in the axial direction) and a drive piston 5 mounted so as to be movable toward the cartridge head 3 (in the axial direction) can be arranged in the cylindrical interior 2 of the cartridge 1.

A cement powder 6 is contained in a first cavity 12 in the cartridge 1, which cavity is delimited on its front side by the cartridge head 3 and on its rear side by the front side of the central piston 4. The cement powder 6 can be pressed into the first cavity 12 and fill it completely (that is to say, except for the interstices between the powder particles of the cement powder 6). The cement powder 6 is particularly preferably compressed in the first cavity 12 and can also be pressurized. A monomer liquid 7 may be arranged in a monomer liquid container 8 in a second cavity 14 in the cartridge 1, which cavity is delimited on its front side by the rear side of the central piston 4 and on its rear side by the front side of the drive piston 5. The monomer liquid container 8 can be a glass ampule or a plastic ampule which can be burst in the second cavity 14 by driving the drive piston

6 forward. The central piston 4 is thereby supported on the cement powder 6 contained in the first cavity 12. The cement powder 6 only becomes flowable when it is continuously or completely wetted with the monomer liquid 7.

A discharge opening 9 is arranged in the cartridge head 3, through which discharge opening a bone cement produced from the cement powder 6 and the monomer liquid 7 can be extruded from the first cavity 12. However, the discharge opening 9 can first be closed by a closure 10 which is permeable to gases but impermeable to the cement powder 6. The discharge opening 9 can be arranged centrally in the cartridge head 3. The cartridge head 3 can taper toward the discharge opening 9 in order to facilitate the discharge of the bone cement out of the first cavity 12.

The monomer liquid container 8 can be burst by driving the drive piston 5 forward, and the monomer liquid 7 in the second cavity 14 can thereby be released. The monomer liquid 7 can subsequently be pressed into the cement powder 6 in the first cavity 12 by further driving the drive piston 5 forward. By stressing the walls of the cartridge 1 and due to elastic deformations of the parts of the device delimiting the second cavity 14, the monomer liquid 7 in the second cavity 12 is subsequently pressurized.

The device has a depressurization device 16 by means of which this pressure in the second cavity 14 can be reduced by discharging portions of the monomer liquid 7 out of the second cavity 12. The depressurization device 16 is arranged on a lateral surface of the cartridge 1. Theoretically, a plurality of identical or different depressurization devices can also be provided in order to reduce the pressure of the monomer liquid 7 in the second cavity 12. The depressurization device 16 is shown as a cross-section in the enlarged detail according to FIG. 4.

A plurality of lines 18 can be arranged in the central piston 4, through which lines the monomer liquid 7 can be pressed from the second cavity 14 into the first cavity 12. The central piston 4 can otherwise be sealed against the inner wall of the cartridge 1 with the aid of circumferential annular seals 20. The seals 20 can be designed as O-rings and consist of an elastic plastic such as rubber. A pore filter 22 may cover the lines 18 on the front side of the central piston 4. The pore filter 22 is permeable to the monomer liquid 7 and gases but impermeable to the cement powder 6. It is thereby prevented that the cement powder 6 is able to penetrate into the lines 18 and close them off when it comes into contact with the monomer liquid 7 therein. A plurality of studs 24 for centering and positioning the monomer liquid container 8 can be arranged on the rear side of the central piston 4. A plurality of studs 26 for centering and mounting the monomer liquid container 8 can likewise be arranged on the front side of the drive piston 5.

The drive piston 5 can have a front seal 28 and a rear seal 30 with which the drive piston 5 is sealed against the inner wall of the cartridge 1. The front seal 28 and the rear seal 30 can be executed as O-rings and consist of an elastic plastic such as rubber. In this way, the drive piston 5 is impermeable to the monomer liquid 7 and preferably also to gases, and also abuts the inner wall of the cartridge 1 so as to be impermeable to the monomer liquid 7 and gases.

A fastening means 32 for fastening an extrusion device (not shown) can be arranged on the rear side of the cartridge 1. The drive piston 5 can be driven forward or driven with a plunger of a connected extrusion device in order to implement a method according to the invention.

Gas supply openings 34 can be arranged in the cartridge wall of the cartridge 1. These are located directly in front of the drive piston 5 in its initial position, which is shown in FIG. 1. The interior 2 of the cartridge 1 is accessible via the gas supply openings 34 for a sterilizing gas such as ethylene oxide. The device can thereby be sterilized and sterilely packaged and stored, which is important for a medical application of the bone cement produced therewith. The gas supply openings 34 are preferably traversed by the drive piston 5 before the monomer liquid container 8 is opened, so that the released monomer liquid 7 cannot escape through the gas supply openings 34.

On the front side of the cartridge 1, a connecting piece with an external thread 36 can be arranged on the cartridge head 3, which connecting piece delimits and extends the discharge opening 9. If necessary, a discharge pipe (not shown) with a matching internal thread can be connected to the external thread 36.

The closure 10 can be connected to a connecting element 38 made of plastic. The connecting element 38 can form a bracket which extends from the closure 10 to a pin 40. The pin 40 serves to lock the depressurization device 16. When the closure 10 is pulled or pushed out of the discharge opening 9, the pin 40 is also automatically pulled out of the depressurization device 16 via the connecting element 38. The depressurization device 16 can thereby be activated automatically by removing the closure 10.

A continuous connection 41 can be provided in the wall of the cartridge 1, by means of which continuous connection the depressurization device 16 is connected or connectible to the second cavity 14 so as to be permeable to the monomer liquid 7. Theoretically, a plurality of continuous connections 41 can also be provided which are connected to the same depressurization device 16 or to a plurality of identical or different depressurization devices. In order to close off the continuous connection 41, a sealing body 42 can be pressed onto the junction of the depressurization device 16 to the continuous connection 41. The sealing body 42 can be realized by a rubber plug, for example. The sealing body 42 can be pressed into the seat by means of a spring guide rod 46 with the aid of a cap 50. A spring 48 can push the cap 50 away from the cartridge 1, and thus push the sealing body 42 away from the continuous connection 41. The spring guide rod 46 can be arranged on the inside of a cap 50 of the depressurization device 16. The spring 48 can be compressed and supported on one side on the outside of the cartridge 1, and on the other side on the inside of the cap 50. The spring 48 can be wound around the spring guide rod 46. The continuous connection 41 can open out, directly adjacent to the central piston 4, into the second cavity 14. It can thereby be ensured that the drive piston 5 does not close the opening into the continuous connection 41 when it is pressed toward the central piston 4.

The depressurization device 16 may further comprise a hollow connecting piece 52 which is preferably designed integrally with the cartridge 1. The pin 40 may extend through a passage 54 in the cap 50 and the hollow connecting piece 52. The cap 50 with the pin 40 can thereby be detachably fixed to the hollow connecting piece 52, and the spring 48 can be held in the compressed state. When the pin 40 is pulled out of the passage 54, the spring 48 pushes the cap 50 away from the cartridge 1, and the sealing body 42 detaches from the continuous connection 41. Pressurized monomer liquid 7 in the second cavity 14 can thereby flow into the depressurization device 16, and the hydrostatic pressure of the monomer liquid 7 in the second cavity 14 can thereby be reduced.

In order for the monomer liquid 7 not to reach the surroundings of the device, the cap 50 can be tightly, but at the same time movably, connected to the connecting piece 52. For this purpose, projections 44 can be provided on the cap 50 and a groove 60 can be provided on the connecting piece 52, wherein the projections 44 engage in the groove 60 and the groove 60 is long enough that the projections 44 are able to move in the groove 60 and the cap 50 is able to lift off from the cartridge 1 far enough that the sealing body 42 is able to detach from the continuous connection 41, but not so far that the cap 50 detaches from the connecting piece 52 or the cap 50 is sits loosely against the connecting piece 52. Alternatively, the groove 60 could also be arranged in the cap 50, and the projections 44 could also be arranged on the connecting piece 52. The interior of the depressurization device 16 hereby internally forms a reservoir for receiving monomer liquid 7, wherein a pulp, a cellulose, or an absorbent material (not shown) can be arranged in the reservoir, with which the monomer liquid 7 can be absorbed and bound.

A guide 56 for guiding the connecting element 38 can be arranged on the outside of the cartridge 1. A stopper 58 can be arranged on the connecting element 38. When the bone cement swells in the first cavity 12 and expands or is pressed into the discharge opening 9 with the central piston 4, the closure 10 is pressed forward (downward in FIG. 1) and thereby presses the connecting element 38 forward until the stopper 58 strikes the guide 56 and blocks further movement. The pin 40 is thereby pulled out of the passage 54, and the depressurization device 16 is activated without the closure 10 needing to already be completely removed from the discharge opening 9. The user recognizes therefrom that the bone cement has been mixed and the device is ready to dispense the bone cement. The closure 10 can then be removed and, if necessary, a discharge pipe can be connected to the external thread 36.

FIGS. 5 to 7 show illustrations of a second device according to the invention for producing a bone cement. FIGS. 5 and 6 show various schematic overall views of the second exemplary device according to the invention, and FIG. 7 shows an enlarged detail of the cross-sectional view according to FIG. 6.

The device according to the second exemplary embodiment of the present invention can also have a tubular cartridge 1 made of a plastic, with a cylindrical interior 2 which is closed on its front side (at the bottom left in FIG. 5 and at the bottom in FIG. 6) by a cartridge head 3. The cartridge head 3 preferably likewise consists of a plastic. A central piston 4 mounted so as to be movable toward the cartridge head 3 (in the axial direction) and a drive piston 5 mounted so as to be movable toward the cartridge head 3 (in the axial direction) can be arranged in the cylindrical interior 2 of the cartridge 1.

A cement powder 6 is contained in a first cavity 12 in the cartridge 1, which cavity is delimited on its front side by the cartridge head 3 and on its rear side by the front side of the central piston 4. The cement powder 6 can be pressed into the first cavity 12 and fill it completely (that is to say, except for the interstices between the powder particles of the cement powder 6). The cement powder 6 is particularly preferably compressed in the first cavity 12 and can also be pressurized. A monomer liquid 7 may be arranged in a monomer liquid container 8 in a second cavity 14 in the cartridge 1, which cavity is delimited on its front side by the rear side of the central piston 4 and on its rear side by the front side of the drive piston 5. The monomer liquid container 8 can be a glass ampule or a plastic ampule which can be burst in the second cavity 14 by driving the drive piston 6 forward. The central piston 4 is thereby supported on the cement powder 6 contained in the first cavity 12. The cement powder 6 only becomes flowable when it is continuously or completely wetted with the monomer liquid 7.

A discharge opening 9 is arranged in the cartridge head 3, through which discharge opening a bone cement produced from the cement powder 6 and the monomer liquid 7 can be extruded from the first cavity 12. However, the discharge opening 9 can first be closed by a closure 10 which is permeable to gases but impermeable to the cement powder 6. The discharge opening 9 can be arranged centrally in the cartridge head 3. The cartridge head 3 can taper toward the discharge opening 9 in order to facilitate the discharge of the bone cement out of the first cavity 12.

The monomer liquid container 8 can be burst by driving the drive piston 5 forward, and the monomer liquid 7 in the second cavity 14 can thereby be released. The monomer liquid 7 can subsequently be pressed into the cement powder 6 in the first cavity 12 by further driving the drive piston 5 forward. By stressing the walls of the cartridge 1 and due to elastic deformations of the parts of the device delimiting the second cavity 14, the monomer liquid 7 in the second cavity 12 is subsequently pressurized. The structure of the device according to the second exemplary embodiment is inasmuch similar to that of the first exemplary embodiment.

The device has a depressurization device 116 by means of which this pressure in the second cavity 14 can be reduced by discharging portions of the monomer liquid 7 out of the second cavity 12, which depressurization device differs, however, from the depressurization device 16 of the first exemplary embodiment. The depressurization device 116 is arranged on a lateral surface of the cartridge 1. Theoretically, a plurality of identical or different depressurization devices can also be provided in order to reduce the pressure of the monomer liquid 7 in the second cavity 12. The depressurization device 116 is shown as a cross-section in the enlarged detail according to FIG. 7.

A plurality of lines 18 can be arranged in the central piston 4, through which lines the monomer liquid 7 can be pressed from the second cavity 14 into the first cavity 12. The central piston 4 can otherwise be sealed against the inner wall of the cartridge 1 with the aid of circumferential annular seals 20. The seals 20 can be designed as O-rings and consist of an elastic plastic such as rubber. A pore filter 22 may cover the lines 18 on the front side of the central piston 4. The pore filter 22 is permeable to the monomer liquid 7 and gases but impermeable to the cement powder 6. It is thereby prevented that the cement powder 6 is able to penetrate into the lines 18 and close them off when it comes into contact with the monomer liquid 7 therein. A plurality of studs 24 for centering and positioning the monomer liquid container 8 can be arranged on the rear side of the central piston 4. A plurality of studs 26 for centering and mounting the monomer liquid container 8 can likewise be arranged on the front side of the drive piston 5.

The drive piston 5 can have a front seal 28 and a rear seal 30 with which the drive piston 5 is sealed against the inner wall of the cartridge 1. The front seal 28 and the rear seal 30 can be executed as O-rings and consist of an elastic plastic such as rubber. In this way, the drive piston 5 is impermeable to the monomer liquid 7 and preferably also to gases, and also abuts the inner wall of the cartridge 1 so as to be impermeable to the monomer liquid 7 and gases.

A fastening means 32 for fastening an extrusion device (not shown) can be arranged on the rear side of the cartridge 1. The drive piston 5 can be driven forward or driven with a plunger of a connected extrusion device in order to implement a method according to the invention.

Gas supply openings 34 can be arranged in the cartridge wall of the cartridge 1. These are located directly in front of the drive piston 5 in its initial position, which is shown in FIG. 1. The interior 2 of the cartridge 1 is accessible via the gas supply openings 34 for a sterilizing gas such as ethylene oxide. The device can thereby be sterilized and sterilely packaged and stored, which is important for a medical application of the bone cement produced therewith. The gas supply openings 34 are preferably traversed by the drive piston 5 before the monomer liquid container 8 is opened, so that the released monomer liquid 7 cannot escape through the gas supply openings 34.

On the front side of the cartridge 1, a connecting piece with an external thread 36 can be arranged on the cartridge head 3, which connecting piece delimits and extends the discharge opening 9. If necessary, a discharge pipe (not shown) with a matching internal thread can be connected to the external thread 36.

The closure 10 can be connected to a connecting element 138 made of plastic. The connecting element 138 can form a bracket which extends from the closure 10 to a fork-shaped supporting body 140. The fork-shaped supporting body 140 serves to lock the depressurization device 116. When the closure 10 is pulled or pushed out of the discharge opening 9, the fork-shaped supporting body 140 is also automatically pulled off from the depressurization device 116 via the connecting element 138. The depressurization device 116 can thereby be activated automatically by removing the closure 10.

A continuous connection 41 can be provided in the wall of the cartridge 1, by means of which continuous connection the depressurization device 116 is connected or connectible to the second cavity 14 so as to be permeable to the monomer liquid 7. Theoretically, a plurality of continuous connections 41 can also be provided which are connected to the same depressurization device 116 or to a plurality of identical or different depressurization devices. In order to close off the continuous connection 41, a sealing body 42 can be pressed onto the junction of the depressurization device 116 to the continuous connection 41. The sealing body 42 can be realized by a rubber plug, for example. The sealing body 42 can be pressed into the seat by means of a spring guide rod 146 with the aid of a cap 150. A spring 148 can push the cap 150 away from the cartridge 1, and thus push the sealing body 42 away from the continuous connection 41. The spring guide rod 146 can be arranged on the inside of a cap 150 of the depressurization device 116. The spring 148 can be pressurized and supported on one side on the outside of the cartridge 1, and on the other side on the inside of the cap 150. The spring 148 can be wound around the spring guide rod 146. The continuous connection 41 can open out, directly adjacent to the central piston 4, into the second cavity 14. It can thereby be ensured that the drive piston 5 does not close the opening into the continuous connection 41 when it is pressed toward the central piston 4.

The depressurization device 116 may further comprise a hollow connecting piece 152 which is preferably designed integrally with the cartridge 1. The fork-shaped supporting body 140 can rest on the outside on a protruding rail 156 of the cap 150 and thereby keep the cap 150 pressed toward cartridge 1, counter to the force of the spring 148. The spring 148 thereby remains compressed, and the sealing body 42 is pressed into the sealing seat, thereby closing the continuous connection 41 into the depressurization device 116. The cap 150 with the fork-shaped supporting body 140 can thereby be pressed onto the hollow connecting piece 152. When the fork-shaped supporting body 140 is removed, the spring 148 pushes the cap 150 away from the cartridge 1, and the sealing body 42 detaches from the continuous connection 41. Pressurized monomer liquid 7 in the second cavity 14 can thereby flow into the depressurization device 116, and the hydrostatic pressure of the monomer liquid 7 in the second cavity 14 can thereby be reduced.

In order for the monomer liquid 7 to not reach the surroundings of the device, the cap 150 can be tightly, but at the same time movably, connected to the connecting piece 152. For this purpose, projections 144 can be provided on the cap 150 and a groove 160 can be provided on the connecting piece 152, wherein the projections 144 engage in the groove 160 and the groove 160 is long enough that the projections 144 are able to move in the groove 160 and the cap 150 is able to lift off from the cartridge 1 far enough that the sealing body 42 is able to detach from the continuous connection 41, but not so far that the cap 150 detaches from the connecting piece 152 or the cap 150 sits loosely against the connecting piece 152. Alternatively, the groove 160 could also be arranged in the cap 150, and the projections 144 could also be arranged on the connecting piece 152. The interior of the depressurization device 116 hereby internally forms a reservoir for receiving monomer liquid 7, wherein a pulp, a cellulose, or an absorbent material (not shown) can be arranged in the reservoir, with which the monomer liquid 7 can be absorbed and bound.

FIGS. 8 to 10 show illustrations of a third device according to the invention for producing a bone cement. FIGS. 8 and 9 show various schematic overall views of the third exemplary device according to the invention, and FIG. 10 shows an enlarged detail of the cross-sectional view according to FIG. 9.

The structure of the third device according to the invention corresponds in large part to that of the first and the second device according to the invention. The third device according to the invention can accordingly likewise have a cartridge 1 having a cylindrical interior 2, which is closed on its front side (at the bottom left in FIG. 8 and at the bottom in FIG. 9) with a cartridge head 3 containing a discharge opening 9. The third device accordingly likewise has a central piston 4 and a drive piston 5 which are arranged axially movably in the cylindrical interior 2 of the cartridge 3. The arrangement of cement powder 6 and monomer liquid 7 in a monomer liquid container 8 in the first cavity 12 and second cavity 14 of the cylindrical interior 2 of the cartridge 1, which cavities are separated from the central piston 4, is also analogous to the first and second exemplary embodiments. The structure of the central piston 4 with the lines 18, the two seals 20, the pore filter 22, and the studs 24 corresponds just as much to that of the first and second exemplary embodiments as does the structure of the drive piston 5 with the studs 26, the front seal 28, and the rear seal 30. Likewise, a fastening means 32, gas supply openings 34, and/or a connecting piece with an external thread 36 can be arranged on the cartridge 1, corresponding to the first and second exemplary embodiments.

The third exemplary embodiment inasmuch resembles the first and the second exemplary embodiments and, for details regarding the structure and the functions of the corresponding parts of the third exemplary embodiment, reference is made to the description of the first and second exemplary embodiments in order to avoid repetitions.

The discharge opening 9 can first be closed by a closure 210 which is permeable to gases but impermeable to the cement powder 6. A cap 238 can be connected to the external thread 36 on the front side of the cartridge 1 via a screw connection 237. The closure 210 can be pushed out of the discharge opening 9 and out of the cap 238 so that the closure 210 projects forward out of the cap 238 when it has moved. Via suitable structuring of the cap 238 on the inside and the closure 210 on the outside, it can be prevented that the closure 210 falls out of the cap 238. The user of the device can recognize, from the projection of the closure 210 out of the cap 238, that the bone cement in the cartridge 1 is completely mixed, because only then the bone cement which has become flowable enables the closure 210 to be driven forward in the discharge opening 9 and in the cap 238. Immediately before application and use of the bone cement, the user can then unscrew the cap 238 and remove the cap 238 with the closure 210 therein.

The monomer liquid container 8 can be burst by driving the drive piston 5 forward, and the monomer liquid 7 in the second cavity 14 can thereby be released. The monomer liquid 7 can subsequently be pressed into the cement powder 6 in the first cavity 12 by further driving the drive piston 5 forward. By stressing the walls of the cartridge 1 and due to elastic deformations of the parts of the device delimiting the second cavity 14, the monomer liquid 7 in the second cavity 12 is subsequently pressurized.

The device according to the third exemplary embodiment also has a depressurization device 216 with which this pressure in the second cavity 14 can be reduced by discharging portions of the monomer liquid 7 out of the second cavity 12, which depressurization device, however, differs from the depressurization devices 16, 116 of the first and second exemplary embodiments. The depressurization device 216 is arranged on a lateral surface of the cartridge 1. Theoretically, a plurality of identical or different depressurization devices can also be provided in order to reduce the pressure of the monomer liquid 7 in the second cavity 12. The depressurization device 216 is shown as a cross-section in the enlarged detail according to FIG. 10.

In the region of the depressurization device 216, the cartridge 1 has a pierceable thin wall 241 which is adjoined by a channel that opens into a reservoir for receiving monomer liquid 7 in the depressurization device 216. The interior of the depressurization device 216 hereby internally forms a reservoir for receiving monomer liquid 7, wherein a pulp, a cellulose, or an absorbent material (not shown) can be arranged in the reservoir, with which the monomer liquid 7 can be absorbed and bound.

In order to pierce the thin wall 241, a spike 242 that is movable against the cartridge 1 can be arranged in the depressurization device 216. If the thin wall 241 is pierced by the spike 242, a continuous connection through the cartridge wall is created in the cartridge wall of the cartridge 1, which connects the second cavity 14 to the reservoir in the depressurization device 216 in a manner which is permeable to the monomer liquid 7. In order for the spike 242 to not close the continuous connection, a channel 254 can be provided in the spike 242, via which the monomer liquid 7 can flow into the reservoir.

Theoretically, a plurality of thin walls 241 with a plurality of spikes 242, which are connected to the same depressurization device 216 or to a plurality of identical or different depressurization devices. The spike 242 can be pushed away from the thin wall 241 by means of a spring guide rod 246 with the aid of a spring 248. The spring guide rod 246 can be arranged on the inside of a cap 250 of the depressurization device 216. The spring 248 can be compressed and supported on one side on the outside of the cartridge 1, and on the other side on the inside of the cap 250. The spring 248 can be wound around the spring guide rod 246. The thin wall 241 can be provided directly next to the central piston 4 as a wall of the second cavity 14. This ensures that the drive piston 5 does not close the opening into the continuous connection pierced by the spike 242 when it is pressed toward the central piston 4.

The depressurization device 216 may further comprise a hollow connecting piece 252 which is preferably designed integrally with the cartridge 1.

In order for the monomer liquid 7 not to reach the surroundings of the device, the cap 250 can be tightly, but at the same time movably, connected to the connecting piece 252. For this purpose, projections 244 can be provided on the cap 250 and a groove 260 can be provided on the connecting piece 252, wherein the projections 244 engage in the groove 260 and the groove 260 is long enough for the projections 244 to be able to move in the groove 260 and for the cap 250 to be able to lift off from the cartridge 1 far enough for the spike 242 not to pierce the thin wall 241, but not so far that the cap 250 detaches from the connecting piece 252 or the cap 250 becomes loose against the connecting piece 252. Alternatively, the groove 260 could also be arranged in the cap 250, and the projections 244 could also be arranged on the connecting piece 252. The cap 250 can be manually pressed against the cartridge 1, counter to the force of the spring 248, so that the spike 242 pierces the thin wall 241 and thereby provides a continuous connection between the second cavity 14 and the reservoir in the depressurization device 216. Pressurized monomer liquid 7 in the second cavity 14 can thereby flow into the depressurization device 216, and the hydrostatic pressure of the monomer liquid 7 in the second cavity 14 can thereby be reduced. The user can recognize, from the closure 210 protruding out of the cap 238, when they wish to manually trigger depressurization. As soon as the closure 210 protrudes out of the cap 238, the user can thus trigger the depressurization device 216 by pressing on the cap 250.

FIGS. 11 and 12 show illustrations of a fourth device according to the invention for producing a bone cement. FIGS. 11 and 12 show various schematic overall views of the fourth exemplary device according to the invention.

The structure of the fourth device according to the invention corresponds in large part to that of the third device according to the invention. The fourth device according to the invention can accordingly likewise have a cartridge 1 having a cylindrical interior 2 which is closed on its front side (at the bottom left in FIG. 11 and at the bottom in FIG. 12) with a cartridge head 3 containing a discharge opening 9. The fourth device accordingly likewise has a central piston 4 and a drive piston 5 which are arranged axially movably in the cylindrical interior 2 of the cartridge 3. The arrangement of cement powder 6 and monomer liquid 7 in a monomer liquid container 8 in the first cavity 12 and second cavity 14 of the cylindrical interior 2 of the cartridge 1, which cavities are separated from the central piston 4, is also analogous to the first, second, and third exemplary embodiments. The structure of the central piston 4 with the lines 18, the two seals 20, the pore filter 22, and the studs 24 corresponds just as much to that of the first and second exemplary embodiments as does the structure of the drive piston 5 with the studs 26, the front seal 28, and the rear seal 30. Likewise, a fastening means 32, gas supply openings 34, and/or a connecting piece with an external thread 36 can be arranged on the cartridge 1, corresponding to the first and second exemplary embodiments.

The fourth exemplary embodiment inasmuch resembles the first and the second exemplary embodiments and, for details regarding the structure and the functions of the corresponding parts of the fourth exemplary embodiment, reference is made to the description of the first and second exemplary embodiments in order to avoid repetitions.

Analogously to the third exemplary embodiment, the discharge opening 9 can first be closed by a closure 210 which is permeable to gases but impermeable to the cement powder 6. A cap 238 can be connected to the external thread 36 on the front side of the cartridge 1 via a screw connection 237. The closure 210 can be pushed out of the discharge opening 9 and out of the cap 238 so that the closure 210 projects forward out of the cap 238 when it has moved. Via suitable structuring of the cap 238 on the inside and the closure 210 on the outside, it can be prevented that the closure 210 falls out of the cap 238. The user of the device can recognize, from the projection of the closure 210 out of the cap 238, that the bone cement in the cartridge 1 is completely mixed, because only then the bone cement which has become flowable enables the closure 210 to be driven forward in the discharge opening 9 and in the cap 238. Immediately before application and use of the bone cement, the user can then unscrew the cap 238 and remove the cap 238 with the closure 210 therein.

The monomer liquid container 8 can be burst by driving the drive piston 5 forward, and the monomer liquid 7 in the second cavity 14 can thereby be released. The monomer liquid 7 can subsequently be pressed into the cement powder 6 in the first cavity 12 by further driving the drive piston 5 forward. By stressing the walls of the cartridge 1 and due to elastic deformations of the parts of the device delimiting the second cavity 14, the monomer liquid 7 in the second cavity 12 is subsequently pressurized.

The device according to the fourth exemplary embodiment also has a depressurization device 316 by means of which this pressure in the second cavity 14 can be reduced by discharging portions of the monomer liquid 7 out of the second cavity 12, which depressurization device, however, differs from the depressurization devices 16, 116, 216 of the first, second, and third exemplary embodiments. The depressurization device 316 is arranged on a lateral surface of the cartridge 1. Theoretically, a plurality of identical or different depressurization devices can also be provided in order to reduce the pressure of the monomer liquid 7 in the second cavity 12.

A continuous connection 41 can be provided in the wall of the cartridge 1, by means of which continuous connection the depressurization device 316 is connected or connectible to the second cavity 14 so as to be permeable to the monomer liquid 7. Theoretically, a plurality of continuous connections 41 can also be provided which are connected to the same depressurization device 316 or to a plurality of identical or different depressurization devices. In order to close off the continuous connection 41, a sealing body 42 can be pressed onto the junction of the depressurization device 316 to the continuous connection 41. The sealing body 42 can be realized by a rubber plug, for example. The sealing body 42 can be pressed into the seat by means of a rod 346 with the aid of a screw cap 350 (or with the aid of a screwable cap 350). The rod 346 can be arranged on the inside of the screw cap 350 of the depressurization device 316. The continuous connection 41 can open out, directly adjacent to the central piston 4, into the second cavity 14. It can thereby be ensured that the drive piston does not close the opening into the continuous connection 41 when it is pressed toward the central piston 4.

The depressurization device 316 may further comprise a hollow connecting piece 352 which is preferably designed integrally with the cartridge 1. The screw cap 350 has an external thread 344, and the connecting piece 352 has a complementary internal thread 360. The screw cap 350 can thereby be screwed away from the connecting piece 352, but preferably not released. The sealing body 42 thereby detaches from the continuous connection 41. Pressurized monomer liquid 7 in the second cavity 14 can thereby flow into the depressurization device 316, and the hydrostatic pressure of the monomer liquid 7 in the second cavity 14 can thereby be reduced.

In order for the monomer liquid 7 not to reach the surroundings of the device, the screw cap 350 can be tightly, but at the same time movably, connected to the connecting piece 352. The interior of the depressurization device 316 hereby internally forms a reservoir for receiving monomer liquid 7, wherein a pulp, a cellulose, or an absorbent material (not shown) can be arranged in the reservoir, with which the monomer liquid 7 can be absorbed and bound.

The user can recognize, from the closure 210 protruding out of the cap 238, when they wish to manually trigger depressurization. As soon as the closure 210 protrudes out of the cap 238, the user can thus trigger the depressurization device 316 by unscrewing or by a rotation in order to release the screw cap 350, and therewith to detach the sealing body 42.

Shown in FIGS. 13 to 15 are illustrations of a fifth device according to the invention for producing a bone cement. FIGS. 13 to 15 show various schematic overall views of the fifth exemplary device according to the invention.

The structure of the fifth device according to the invention corresponds in large part to that of the first and the second device according to the invention, and also to the third and fourth device according to the invention. The fifth device according to the invention can accordingly likewise have a cartridge 1 having a cylindrical interior 2, which is closed on its front side (at the bottom left in FIGS. 13 and 15 and at the bottom in FIG. 14) with a cartridge head 3 containing a discharge opening 9. The fifth device accordingly likewise has a central piston 4 and a drive piston 5 which are arranged axially movably in the cylindrical interior 2 of the cartridge 3. The arrangement of cement powder 6 and monomer liquid 7 in a monomer liquid container 8 in the first cavity 12 and second cavity 14 of the cylindrical interior 2 of the cartridge 1, which cavities are separated from the central piston 4, is also analogous to the first and second exemplary embodiments. The structure of the central piston 4 with the lines 18, the two seals 20, the pore filter 22, and the studs 24 corresponds just as much to that of the first and second exemplary embodiments as does the structure of the drive piston 5 with the studs 26, the front seal 28, and the rear seal 30. Likewise, a fastening means 32, gas supply openings 34, and/or a connecting piece with an external thread 36 can be arranged on the cartridge 1, corresponding to the first and second exemplary embodiments.

In this respect, the fifth exemplary embodiment resembles the first and the second exemplary embodiments and, for details regarding the structure and the functions of the corresponding parts of the third exemplary embodiment, reference is made to the description of the first and second exemplary embodiments in order to avoid repetitions.

Analogously to the third and fourth exemplary embodiment, the discharge opening 9 can first be closed by a closure 210 which is permeable to gases but impermeable to the cement powder 6. A cap 238 can be connected to the external thread 36 on the front side of the cartridge 1 via a screw connection 237. The closure 210 can be pushed out of the discharge opening 9 and out of the cap 238 so that the closure 210 projects forward out of the cap 238 when it has moved. Via suitable structuring of the cap 238 on the inside and the closure 210 on the outside, it can be prevented that the closure 210 falls out of the cap 238. The user of the device can recognize, from the projection of the closure 210 out of the cap 238, that the bone cement in the cartridge 1 is completely mixed, because only then the bone cement which has become flowable enables the closure 210 to be driven forward in the discharge opening 9 and in the cap 238. Immediately before application and use of the bone cement, the user can then unscrew the cap 238 and remove the cap 238 with the closure 210 therein.

The monomer liquid container 8 can be burst by driving the drive piston 5 forward, and the monomer liquid 7 in the second cavity 14 can thereby be released. The monomer liquid 7 can subsequently be pressed into the cement powder 6 in the first cavity 12 by further driving the drive piston 5 forward. By stressing the walls of the cartridge 1 and due to elastic deformations of the parts of the device delimiting the second cavity 14, the monomer liquid 7 in the second cavity 12 is subsequently pressurized.

The device according to the fifth exemplary embodiment also has a depressurization device 416 by means of which this pressure in the second cavity 14 can be reduced by discharging portions of the monomer liquid 7 out of the second cavity 12, which depressurization device, however, differs from the depressurization devices 16, 116, 216, 316 of the first, second, third, and fourth exemplary embodiments. The depressurization device 416 is arranged on a lateral inner surface of the cartridge 1. Theoretically, a plurality of identical or different depressurization devices can also be provided in order to reduce the pressure of the monomer liquid 7 in the second cavity 12.

In the region of the depressurization device 416, the cartridge 1 has a groove 441 over which the front seal 28 of the drive piston 5 is pushed when the drive piston 5 is pressed far enough toward the central piston 4. A connection is thereby created which is permeable to the monomer liquid between the second cavity 14 and a reservoir between the outside of the drive piston 5 and the inner wall of the cartridge 1, which reservoir is sealed on its rear side by the second seal 30 of the drive piston 5. The drive piston 5 can have at least one recess for receiving monomer liquid 7 on the shell surface thereof which faces the inner wall of the cartridge 1. The reservoir can thereby be enlarged. The reservoir is provided for receiving monomer liquid 7, wherein a pulp, a cellulose, or an absorbent material (not shown) can be arranged in the reservoir, by means of which the monomer liquid 7 can be absorbed and bound. The reservoir is opened automatically by traversing the groove 441 with the front seal 28, and an automatic relief of the hydrostatic pressure of the monomer liquid 7 in the second cavity 14 is thereby achieved.

FIGS. 16 and 17 show illustrations of a sixth device according to the invention for producing a bone cement, which is very similar to the fourth device according to the invention. FIGS. 16 and 17 show various schematic overall views of the fourth exemplary device according to the invention.

The structure of the sixth device according to the invention corresponds accordingly in large part to that of the fourth device according to the invention. The sixth device according to the invention can accordingly likewise have a cartridge 1 having a cylindrical interior 2, which is closed on its front side (at the bottom left in FIG. 16 and at the bottom in FIG. 17) with a cartridge head 3 containing a discharge opening 9. The sixth device accordingly likewise has a central piston 4 and a drive piston which are arranged axially movably in the cylindrical interior 2 of the cartridge 3. The arrangement of cement powder 6 and monomer liquid 7 in a monomer liquid container 8 in the first cavity 12 and second cavity 14 of the cylindrical interior 2 of the cartridge 1, which cavities are separated from the central piston 4, is also analogous to the other exemplary embodiments. The structure of the central piston 4 with the lines 18, the two seals 20, the pore filter 22, and the studs 24 corresponds just as much to that of the first and second exemplary embodiments as does the structure of the drive piston 5 with the studs 26, the front seal 28, and the rear seal 30. Likewise, a fastening means 32, gas supply openings 34, and/or a connecting piece with an external thread 36 can be arranged on the cartridge 1, corresponding to the first and second exemplary embodiments.

In this respect, the sixth exemplary embodiment resembles the first and the second exemplary embodiments and, for details regarding the structure and the functions of the corresponding parts of the sixth exemplary embodiment, reference is made to the description of the first and second exemplary embodiments in order to avoid repetitions.

Analogously to the fourth exemplary embodiment, the discharge opening 9 can first be closed by a closure 210 which is permeable to gases but impermeable to the cement powder 6. A cap 238 can be connected to the external thread 36 on the front side of the cartridge 1 via a screw connection 237. The closure 210 can be pushed out of the discharge opening 9 and out of the cap 238 so that the closure 210 projects forward out of the cap 238 when it has moved. Via suitable structuring of the cap 238 on the inside and the closure 210 on the outside, it can be prevented that the closure 210 falls out of the cap 238. The user of the device can recognize, from the projection of the closure 210 out of the cap 238, that the bone cement in the cartridge 1 is completely mixed, because only then the bone cement which has become flowable enables the closure 210 to be driven forward in the discharge opening 9 and in the cap 238. Immediately before application and use of the bone cement, the user can then unscrew the cap 238 and remove the cap 238 with the closure 210 therein.

The monomer liquid container 8 can be burst by driving the drive piston 5 forward, and the monomer liquid 7 in the second cavity 14 can thereby be released. The monomer liquid 7 can subsequently be pressed into the cement powder 6 in the first cavity 12 by further driving the drive piston 5 forward. By stressing the walls of the cartridge 1 and due to elastic deformations of the parts of the device delimiting the second cavity 14, the monomer liquid 7 in the second cavity 12 is subsequently pressurized.

The device according to the sixth exemplary embodiment also has a depressurization device 516 with which this pressure in the second cavity 14 can be reduced by discharging portions of the monomer liquid 7 out of the second cavity 12, which depressurization device, however, differs from the depressurization devices 16, 116, 216, 316, 416 of the other exemplary embodiments, yet is nonetheless very similar in terms of function to the depressurization device 316 of the fourth exemplary embodiment. The depressurization device 516 is arranged on a lateral surface of the cartridge 1. Theoretically, a plurality of identical or different depressurization devices can also be provided in order to reduce the pressure of the monomer liquid 7 in the second cavity 12.

A continuous connection 41 can be provided in the wall of the cartridge 1, by means of which continuous connection the depressurization device 516 is connected or connectible to the second cavity 14 so as to be permeable to the monomer liquid 7. Theoretically, a plurality of continuous connections 41 can also be provided which are connected to the same depressurization device 516 or to a plurality of identical or different depressurization devices. In order to close off the continuous connection 41, a sealing body 42 can be pressed onto the junction of the depressurization device 516 to the continuous connection 41. The sealing body 42 can be realized by a rubber plug, for example. The sealing body 42 can be pressed into the seat by means of a rod 546 with the aid of a screw 550. The rod 546 is the tip of the screw 550. The continuous connection 41 can open out, directly adjacent to the central piston 4, into the second cavity 14. It can thereby be ensured that the drive piston 5 does not close the opening into the continuous connection 41 when it is pressed toward the central piston 4.

The depressurization device 516 may further comprise a hollow connecting piece 552 having a strut 553 for mechanical stabilization, which is preferably designed integrally with the cartridge 1. The screw 550 has an external thread 544, and the connecting piece 552 has a complementary internal thread 560. The screw 550 can thereby be screwed into the connecting piece 552, but preferably not separated. By releasing the screw 550, the sealing body 42 detaches from the continuous connection 41. Pressurized monomer liquid 7 in the second cavity 14 can thereby flow into the depressurization device 516, and the hydrostatic pressure of the monomer liquid 7 in the second cavity 14 can thereby be reduced.

In order for the monomer liquid 7 not to reach the surroundings of the device, the screw 550 can be tightly connected to the connecting piece 352. The interior of the depressurization device 516 hereby internally forms a reservoir for receiving monomer liquid 7, wherein a pulp, a cellulose, or an absorbent material (not shown) can be arranged in the reservoir, with which the monomer liquid 7 can be absorbed and bound.

The user can recognize, from the closure 210 protruding out of the cap 238, when they wish to manually trigger depressurization. As soon as the closure 210 protrudes out of the cap 238, the user can thus trigger the depressurization device 516 by unscrewing or by a rotation in order to release the screw 550, and thereby to detach the sealing body 42.

The features of the invention disclosed in the preceding description, as well as the claims, Figures, and exemplary embodiments, may be essential both individually and in any combination for realizing the invention in its various embodiments.

LIST OF REFERENCE CHARACTERS

1 Cartridge
2 Interior
3 Cartridge head
4 Central piston
5 Drive piston
6 Cement powder
7 Monomer liquid
8 Monomer liquid container
9 Discharge opening
10, 210 Closure
12 First cavity
14 Second cavity
16, 116, 216, 316, 416, 516 Depressurization device
18 Line
20 Seal
22 Pore filter
24, 26 Stud
28 Front seal

30 Rear seal
32 Fastening means
34 Gas supply opening
36 External thread
38, 138 Connecting element
40 Pin
41 Connection
42 Sealing body
44, 144, 244 Protrusion
46, 146, 246 Spring guide rod
48, 148, 248 Spring
50, 150, 250 Cap
52, 152, 252, 352, 552 Connecting piece
54 Passage
56 Guide
58 Stopper
60, 160, 260 Groove
140 Supporting body
156 Rail
237 Screw connection
238 Cap
241 Thin wall
242 Spike
254 Channel
344 External thread
346 Rod
350 Screw cap
360 Internal thread
441 Groove
544 External thread
546 Rod
550 Screw
553 Strut
560 Internal thread
The invention claimed is:

1. A method for producing a bone cement, wherein the bone cement is produced from a cement powder and a monomer liquid using a device for mixing the bone cement, the device comprising
  a cartridge having a cylindrical interior,
  the cement powder for producing the bone cement,
  the monomer liquid for producing the bone cement, wherein the monomer liquid is contained in a monomer liquid container,
  a cartridge head having a discharge opening for expelling the bone cement, wherein the cartridge head closes off the cylindrical interior of the cartridge at a front side of the cartridge, except for the discharge opening,
  a closure, wherein the closure is permeable to gases and impermeable to powder particles of the cement powder, and wherein the closure is arranged in the discharge opening and is removable from the discharge opening,
  a drive piston, wherein the drive piston is impermeable to gases and the monomer liquid, wherein the drive piston is arranged movable towards the cartridge head in the cylindrical interior of the cartridge,
  a central piston, wherein the central piston is permeable to gases and the monomer liquid and impermeable to powder particles of the cement powder, wherein the central piston is arranged movably in the cylindrical interior of the cartridge towards the cartridge head and is arranged between the drive piston and the cartridge head, wherein
  the central piston separates the cylindrical interior of the cartridge into a first cavity and a second cavity, wherein the first cavity is delimited on a front side by the cartridge head and the closure, opposite thereto by the central piston, and laterally by an inner wall of the cartridge, and wherein the second cavity is delimited on a front side by the central piston, opposite thereto by the drive piston, and laterally by the inner wall of the cartridge, wherein the cement powder is arranged in the first cavity, and wherein the monomer liquid container is arranged in the second cavity,
wherein the method comprises the following steps:
  A) moving the drive piston toward the cartridge head,
  B) opening the monomer liquid container or rupturing the monomer liquid container via the movement of the drive piston toward the cartridge head, and thereby releasing the monomer liquid in the second cavity,
  C) expelling residual gases through the central piston, through the cement powder, and through the closure, into the surroundings of the device, by means of the movement of the drive piston,
  D) injecting the monomer liquid through the central piston into the cement powder, via further movement of the drive piston toward the cartridge head,
  E) displacing gases between the powder particles with the inflowing monomer liquid, wherein the gases escape through the closure into the surroundings of the device,
  F) wetting the powder particles of the cement powder, and
  G) depressurizing the second cavity after steps A) to F), wherein the second cavity is depressurized by partially removing the monomer liquid contained in the second cavity.

2. The method according to claim 1, characterized in that the pressure in the second cavity is reduced via the depressurizing by at least 30% by the depressurization.

3. The method according to claim 1, characterized in that the movement of the drive piston toward the cartridge head is driven by an external extrusion device, wherein the device for mixing the bone cement is preferably inserted into the extrusion device and/or is attached to the extrusion device.

4. The method according to claim 1, characterized in that, in step F), the powder particles of the cement powder are completely wetted by the monomer liquid.

5. The method according to claim 1, characterized by the chronological steps of
  H) removing the closure from the cartridge head after step G), and
  I) extruding the bone cement out of the first cavity and through the discharge opening via a movement of the central piston toward the cartridge head, wherein the central piston is pressed by the drive piston toward the cartridge head.

6. The method according to claim 1, characterized in that the depressurization in step G) takes place via manual or automatic actuation of a depressurization device of the device for mixing the bone cement, wherein the automatic actuation of the depressurization device is triggered by a movement of the drive piston, and/or
  is triggered by a movement of the closure out of the cartridge head, and is driven by the movement of the closure out of the cartridge head, and/or
  during the depressurization in step G), the monomer liquid is discharged into a reservoir outside the cartridge or in the cartridge wall, wherein the reservoir is sealed tightly to the outside for the monomer liquid, or
  during the depressurization in step G), the monomer liquid is conducted into a reservoir within the drive piston, into a reservoir on the side of the drive piston opposite the second cavity, and/or into a reservoir laterally between the drive piston and the cartridge, wherein, in the latter case, the monomer liquid is conducted via at least one groove in an inner wall of the cartridge, past a front sealing ring of the drive piston, into the reservoir laterally between the drive piston and the cartridge, when a front sealing ring of the drive piston is pushed over or onto the at least one groove.

7. The method according to claim 1, characterized in that during the depressurization in step G), the monomer liquid is not conducted into the first cavity, is conducted into at least one reservoir separate from the first cavity, wherein the at least one reservoir is arranged outside the cartridge, within the cartridge wall, within the drive piston, on the side of the drive piston opposite the second cavity, and/or laterally between the drive piston and the cartridge, and/or during depressurization in step G), the second cavity is filled with the open or ruptured monomer liquid container and with residues of the monomer liquid.

8. The method according to claim 1, characterized in that the bone cement is a pasty polymethyl methacrylate bone cement.

9. A device for mixing a bone cement, the device comprising a cartridge having a cylindrical interior,
a cement powder for producing the bone cement,
a monomer liquid for producing the bone cement, wherein the monomer liquid is contained in
a monomer liquid container,
a cartridge head having a discharge opening for expelling the bone cement, wherein the cartridge head closes off a cylindrical interior of the cartridge at a front side of the cartridge, except for the discharge opening,
a closure, wherein the closure is permeable to gases and impermeable to powder particles of the cement powder, and wherein the closure is arranged in the discharge opening and is removable from the discharge opening,
a drive piston, wherein the drive piston is impermeable to gases and the monomer liquid,
wherein the drive piston is arranged movably towards the cartridge head in the cylindrical interior of the cartridge,
a central piston, wherein the central piston is permeable to gases and the monomer liquid and impermeable to the powder particles of the cement powder, wherein the central piston is arranged movably in the cylindrical interior of the cartridge toward the cartridge head and is arranged between the drive piston and the cartridge head, wherein the central piston separates the cylindrical interior of the cartridge into a first cavity and a second cavity, wherein the first cavity is delimited on a front side by the cartridge head and the closure, opposite thereto by the central piston and laterally by an inner wall of the cartridge, and wherein the second cavity is delimited on a front side by the central piston, opposite thereto by the drive piston, and laterally by the inner wall of the cartridge,
wherein the cement powder is arranged in the first cavity and wherein the monomer liquid container is arranged in the second cavity, and
a depressurization device by means of which monomer liquid is dischargeable from the second cavity or is dischargeable from the second cavity and receivable, or by means of which the volume of the second cavity is increasable, wherein the depressurization device is connected or connectible to the second cavity.

10. The device according to claim 9, characterized in that the depressurization device is connected to the second cavity via at least one continuous connection in a wall of the cartridge, wherein the at least one continuous connection is closed or closeable with at least one sealing body, wherein the at least one sealing body is pressed against the at least one continuous connection with an externally manually operable screw or screw cap, with a rod, or with a spring guide rod.

11. The device according to claim 10, characterized in that the at least one sealing body, or a rod or a spring guide rod pressing onto the at least one sealing body, is liftable from the at least one continuous connection with a spring; the spring presses the spring guide rod, which presses the at least one sealing body against the at least one continuous connection, away from the at least one continuous connection, wherein the spring is locked with a pin or with a fork-shaped supporting body, and the pin or the fork-shaped supporting body is firmly connected to the closure such that, when the closure moves out of the discharge opening, the pin or the fork-shaped supporting body is also automatically removed from the depressurization device, and the locking of the spring is thereby released.

12. The device according to claim 9, characterized in that at least one continuous connection is arranged in the cartridge wall and connects the cylindrical interior of the cartridge to the external surroundings, wherein the at least one continuous connection is reversibly closed or closable, and wherein the reversible closure of the at least one continuous connection takes place via a sealing body which is pressed against the at least one continuous connection by a screw or a screw cap, wherein the screw or the screw cap is manually rotatable from the outside.

13. The device according to claim 9, characterized in that the depressurization device has a spike for piercing a wall of the cartridge in the region of the second cavity, wherein the spike is movably mounted against the cartridge, wherein the spike is a hollow spike with a cannula that is connected to a reservoir for receiving the monomer liquid, or, after piercing the wall of the cartridge, the spike is retractable manually or by a spring such that it exposes a passage pierced with the spike to discharge the monomer liquid from the second cavity, wherein the wall is thinner in the region of the spike than in the rest of the cartridge.

14. The device according to claim 9, characterized in that the drive piston is sealed with at least one sealing ring against the inner wall of the cartridge, is sealed with two sealing rings against the inner wall of the cartridge, wherein the two sealing rings are spaced apart from one another by at least 5 mm, in a direction parallel to the cylinder axis of the cylindrical interior, wherein at least one groove is arranged in an inner wall of the cartridge which delimits the second cavity, wherein the at least one groove in a direction parallel to the cylinder axis of the cylindrical interior is at least as long as the diameter of a front sealing ring of the at least one sealing ring arranged closest toward the cartridge head, or wherein the at least one groove parallel to the cylinder axis of the cylindrical interior is at least half as long as the front sealing ring and is at least 4 mm wide along the cylinder shell.

* * * * *